(12) United States Patent
Haefner et al.

(10) Patent No.: US 8,491,491 B2
(45) Date of Patent: Jul. 23, 2013

(54) RESPIRATION MEASUREMENTS AND DOSIMETRY CONTROL IN INHALATION TESTING SYSTEMS

(75) Inventors: Paul A. Haefner, Circle Pines, MN (US); Loell Boyce Moon, Ham Lake, MN (US); Steve Hachtman, Excelsior, MN (US); Scott R. Tiesma, Ramsey, MN (US); Gary Pritchard, Macungie, PA (US)

(73) Assignee: Data Sciences International, Inc., St. Paul, MN (US)

( * ) Notice: Subject to any disclaimer, the term of this patent is extended or adjusted under 35 U.S.C. 154(b) by 699 days.

(21) Appl. No.: 12/715,503

(22) Filed: Mar. 2, 2010

(65) Prior Publication Data

US 2011/0218450 A1 Sep. 8, 2011

(51) Int. Cl.
*A61B 5/08* (2006.01)
*A01K 1/03* (2006.01)
*A61M 31/00* (2006.01)

(52) U.S. Cl.
USPC ............ 600/532; 119/420; 119/421; 604/66; 604/503; 600/529

(58) Field of Classification Search
USPC ............ 600/529, 532; 119/416–421; 702/19; 604/66, 503
See application file for complete search history.

(56) References Cited

U.S. PATENT DOCUMENTS

| | | | | |
|---|---|---|---|---|
| 2,970,143 A * | 1/1961 | Fried et al. | | 540/37 |
| 3,690,143 A * | 9/1972 | Day | | 73/1.73 |
| 4,216,741 A * | 8/1980 | Moss | | 119/420 |
| 4,305,347 A * | 12/1981 | Hemenway et al. | | 119/420 |
| 4,348,985 A * | 9/1982 | Leong | | 119/420 |
| 4,520,808 A * | 6/1985 | LaBauve | | 128/200.14 |
| 4,721,060 A * | 1/1988 | Cannon et al. | | 119/420 |
| 4,841,982 A * | 6/1989 | Nikiforov et al. | | 600/529 |
| 5,379,777 A * | 1/1995 | Lomask | | 600/529 |
| 5,887,586 A * | 3/1999 | Dahlback et al. | | 128/204.22 |
| 6,076,015 A * | 6/2000 | Hartley et al. | | 607/20 |
| 6,287,264 B1 * | 9/2001 | Hoffman | | 600/538 |
| 6,679,259 B2 | 1/2004 | Heesch | | |
| 6,902,532 B2 * | 6/2005 | Lomask | | 600/529 |
| 6,904,912 B2 | 6/2005 | Roy et al. | | |
| 7,004,163 B2 | 2/2006 | Nashed | | |
| 7,104,962 B2 * | 9/2006 | Lomask et al. | | 600/529 |
| 7,290,544 B1 | 11/2007 | Sarela et al. | | |
| 7,377,276 B2 * | 5/2008 | Roy et al. | | 128/203.14 |
| 7,451,760 B2 | 11/2008 | Denyer et al. | | |
| 7,527,052 B2 | 5/2009 | Hickle et al. | | |
| 7,603,170 B2 * | 10/2009 | Hatlestad et al. | | 600/547 |

(Continued)

*Primary Examiner* — Navin Natnithithadha
*Assistant Examiner* — Michael R Bloch
(74) *Attorney, Agent, or Firm* — Fish & Richardson P.C.

(57) ABSTRACT

Inhalation measurement systems and methods enable, during inhalant exposure, substantially real-time respiratory measurements of a test subject using techniques that obtain measurements of respiration directly from that test subject, instead of from inhalation chamber parameter measurements. Direct test subject respiratory measurements may be, by way of example only, impedance measurements. These respiratory measurements taken directly from the test subject may be transmitted, wirelessly for example, for processing during the course of the test to a processing system to determine a cumulative volume of inhalant inspired by the test subject. From that, a cumulative amount of inhalant (or dose) inspired by the test subject may be determined during the course of the inhalation compound test. In addition, a calibration procedure may be performed before the inhalant exposure to provide correlation needed to translate chest and/or abdominal wall expansion measurements, made during the test, into lung volume measurements.

21 Claims, 12 Drawing Sheets

U.S. PATENT DOCUMENTS

Figure 1:
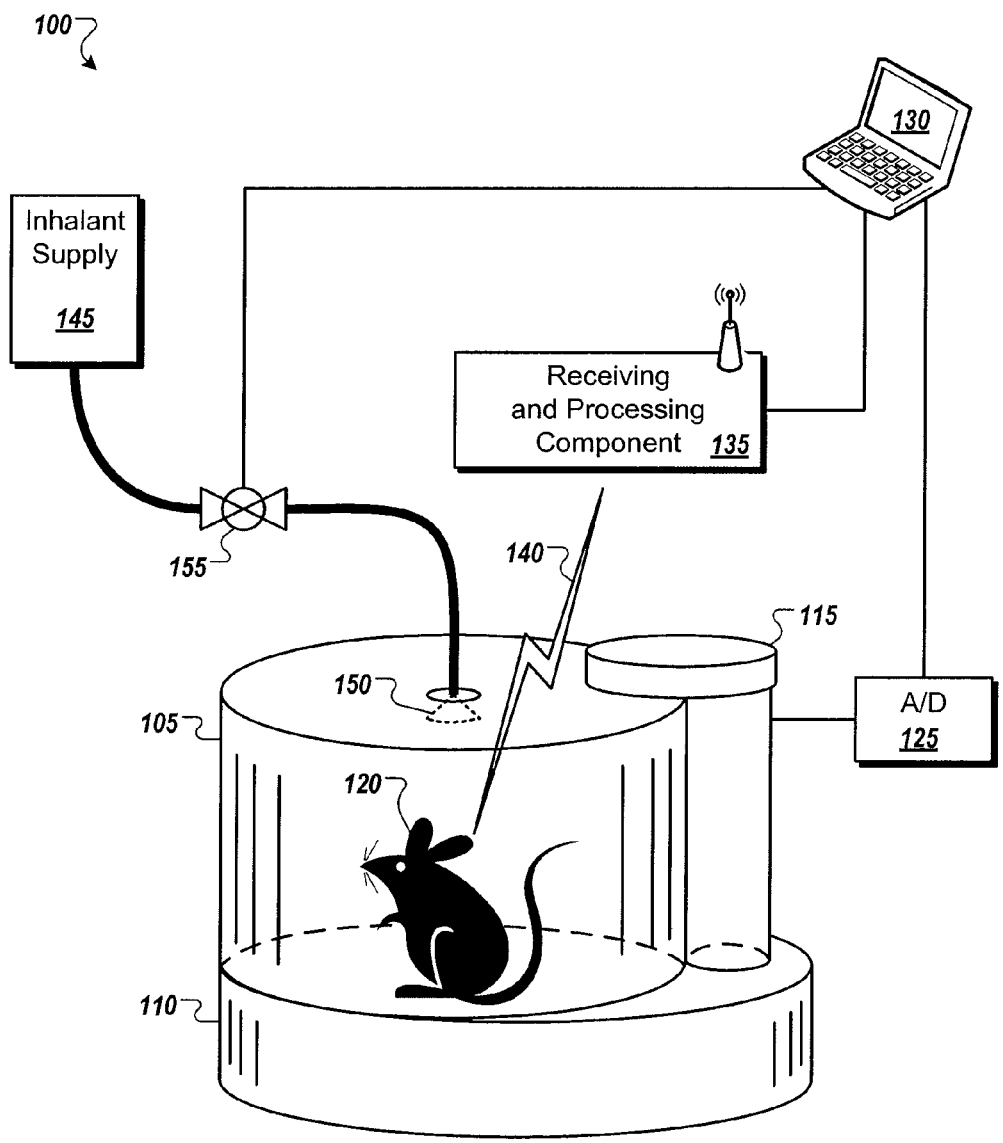

| | | | |
|---|---|---|---|
| 7,704,211 B1* | 4/2010 | Koh ............................... | 600/486 |
| 8,066,646 B2* | 11/2011 | Sheehan et al. ............... | 600/529 |
| 8,221,329 B2* | 7/2012 | Hartings et al. ............... | 600/535 |
| 8,328,729 B2* | 12/2012 | Reynolds et al. .............. | 600/538 |
| 2002/0103443 A1* | 8/2002 | Roy et al. ....................... | 600/532 |
| 2003/0055354 A1* | 3/2003 | Roy et al. ....................... | 600/532 |
| 2003/0125633 A1* | 7/2003 | Hartings et al. ............... | 600/532 |
| 2005/0205090 A1* | 9/2005 | Roy et al. ................. | 128/203.18 |
| 2005/0251232 A1* | 11/2005 | Hartley et al. ................... | 607/96 |
| 2006/0241513 A1* | 10/2006 | Hatlestad et al. ............. | 600/547 |
| 2009/0012395 A1* | 1/2009 | Reynolds et al. ............. | 600/437 |
| 2009/0118626 A1* | 5/2009 | Moon et al. .................... | 600/484 |
| 2009/0120435 A1 | 5/2009 | Slessarev et al. | |
| 2009/0124867 A1 | 5/2009 | Hirsh et al. | |
| 2009/0223460 A1* | 9/2009 | Starr et al. .................... | 119/420 |

* cited by examiner

```
                                    ┌─────────┐
                                    │  Start  │
   900                              └────┬────┘
                                         ▼
              ┌────────────────────────────────────────┐
              │   Supply Airborne Inhalant in          │
         ┌───▶│   Chamber Airway            905        │
         │    └────────────────┬───────────────────────┘
         │                     ▼
         │    ┌────────────────────────────────────────┐
         │    │   Measure Impedance Values as          │
         │    │   Test Subject Breathes     910        │
         │    └────────────────┬───────────────────────┘
         │                     ▼
         │    ┌────────────────────────────────────────┐
         │    │   Apply Conversion Factor              │
         │    │   to Determine                         │
         │    │   Breath Volume             915        │
         │    └────────────────┬───────────────────────┘
         │                     ▼
         │    ┌────────────────────────────────────────┐
         │    │   Determine Inspired                   │
         │    │   Dosage                    920        │
         │    └────────────────┬───────────────────────┘
         │                     ▼
         │    ┌────────────────────────────────────────┐
         │    │   Totalize Inspired                    │
         │    │   Dosage                    925        │
         │    └────────────────┬───────────────────────┘
         │                     ▼
         │               No  ╱Total Inspired Dosage >=╲
         │    ┌─────────────◁ Predetermined Total      ▷
         │    │                ╲ Dosage?          930 ╱
         │    ▼                          │
         │  ┌──────────────────┐         │ Yes
         │  │ Determine Inspired│        │
         │  │ Dosage       935 │        │
         │  └────────┬─────────┘        │
         │          ▼                    │
         │  No   ╱ Particle Size ╲       │
         │◁─────◁ Adjustment      ▷     │
         │       ╲ Needed?   940 ╱      │
         │              │                │
         │           Yes│                ▼
         │              ▼         ┌──────────────────┐
         │   ┌────────────────┐   │ Trigger Event    │
         └───│ Modify Inhalant │   │            950  │
             │ Particle Size   │   └────────┬─────────┘
             │           945  │            ▼
             └────────────────┘        ┌─────────┐
                                       │   End   │
                                       └─────────┘
```

FIG. 9

RESPIRATION MEASUREMENTS AND DOSIMETRY CONTROL IN INHALATION TESTING SYSTEMS

TECHNICAL FIELD

This invention relates to respiratory measurements and dosimetry control in inhalation substance (e.g., drug) testing systems.

BACKGROUND

Inhalation studies are generally performed using inhalant systems. These studies are typically performed by exposing one or more animals to either an organic or inorganic inhalant inside an inhalant chamber. Various implementations of such a system maintain the chamber environment using a proportional integral derivative (PID) controller and measurements of pressure, temperature, humidity, air flow into and air flow out of the chamber. In some inhalation systems, the animal's respiratory volume and respiratory rate can be calculated from inhalant chamber measurements such as temperature, humidity and pressure variations. The individual breath dose can then be determined by multiplying the average inhalant concentration during each breath by the calculated respiratory volume for that same breath. The accumulated dose for the entire exposure may then be determined by summing the product of the individual breath volumes and its average inhalant concentration.

Alternatively, direct, near real-time measurements of animal respiratory parameters may be made under conditions similar to those during the inhalation study some time prior to the actual study. These measurements may then be multiplied by the average inhalant concentration to infer an individual breath dose and ultimately the accumulated dose during exposure.

Respiratory volume calculations using chamber measurements are susceptible to errors. Chamber baseline pressure changes may occur due to differing degrees of neck seal of test animals. Chamber pressure may also vary when a nebulizer used to introduce the inhalant into the chamber switches on and off as it regulates the inhalant concentration. These non-respiratory related variations in baseline pressure have a large influence on the measured pressure variations and therefore on the calculated respiratory volume.

The equations used to calculate respiratory volume from pressure variations present another potential error source. Assumptions that may or may not be valid during the inhalation study may be made for each equation. For example, the ideal gas law neglects molecular size and intermolecular attractions and thus is most accurate for a monoatomic gas at high temperatures and low pressures. By definition, the nebulizer is creating an inhalant which is non-monoatomic therefore inaccuracies are introduced.

Direct near real-time measurements of animal respiratory patterns prior to the actual study avoid the inaccuracies associated with calculated respiratory parameters using inhalation chamber measurements; however, this method is not without its own error sources. Animal respiratory patterns may change significantly throughout the course of a study. Alterations in respiratory rate, volume or both may occur as a result of metabolic demand, level of anesthesia, if used in the study, or the amount or type of inhalant used. These respiratory changes can create large levels of uncertainty with respect to dosimetry. This uncertainty may result in variable results and ultimately poor reproducibility of scientific experiments.

Direct respiratory measurements using a breath analyzer such as a pneumotachograph can provide real time respiratory measurements and thus improve dosimetry accuracy; however, these measurements are often impractical because inhalants often clog the breath analyzer screens. Additionally, many inhalant compounds are biohazards; thus, thorough cleaning and/or decontamination of the breath analyzer is required. This can be a difficult and lengthy procedure that can potentially damage or degrade the highly sensitive equipment.

SUMMARY

This document discloses inhalation measurement systems and methods that enable, during inhalant exposure, substantially real-time respiratory measurements of a test subject using various techniques that obtain measurements of respiration directly from that test subject instead of from inhalation chamber parameter measurements. Direct test subject measurements include, but are not limited to, respiratory inductance plethysmography (RIP), impedance measurements, elastomeric plethysmography, and other chest and/or abdominal expansion measurement techniques.

These respiratory measurements taken directly from the test subject may be transmitted, wirelessly for example, for processing during the course of the test to a processing system to determine a cumulative volume of inhalant inspired by the test subject. From that, a cumulative amount of inhalant (or dose) inspired by the test subject may be determined during the course of the inhalation compound test. By using respiratory measurement techniques that take measurements directly from the test subject during the course of a test or study, it is possible to avoid the use of techniques that rely on measurements (for example, pressure measurements using a pneumotachograph) of the atmosphere within the test chamber including the inhalant in that atmosphere. As such, it is possible to avoid disadvantages of using such atmospheric measurement techniques, for example, time-consuming or oftentimes expensive sterilization procedures required to reuse the system for the next test, and/or having to perform difficult cleaning operations following a test to clean filters for example that are interposed between the atmosphere of the test chamber and the atmospheric measurement system.

In addition, it is desirable to perform a calibration procedure before the disclosed inhalant exposure. A calibration provides the correlation needed to translate chest and/or abdominal wall expansion measurements, made during the test, into lung volume measurements. As such, in a calibration procedure, temporally independent of dosing, a standard respiration method/technology may be used independently or in cooperation with the atmospheric measurement system to obtain a respiratory volume measurement (for example, a volume measurement for each breath of the test subject), while at the same time chest and/or abdominal wall expansion measurements are taken directly from the test subject using the same measurement technique that will later be used during dosing. Because no inhalant need be introduced into the test chamber during the calibration process, the disadvantages of using the atmospheric measurement system discussed previously are not present.

In one aspect, a method and corresponding apparatus are provided for performing an inhalation test on a test subject. The method includes performing a calibration procedure comprising a) collecting respiration-related measurements for each of multiple respiration cycles from the test subject using a sensing device applied directly to the test subject, b) collecting corresponding respiration volume measurements for each of the multiple respiration cycles of the test subject by sensing atmospheric changes of a volume within a chamber in which the test subject is at least partially confined, and c) using the collected respiration-related and respiration volume measurements to calculate a calibration formula that correlates respiration-related measurements collected using the sensing device applied directly to the test subject to respiration volume measurements. The method also includes performing an inhalation test on the test subject during which inhalation test the test subject is at least partially confined within a test chamber and an inhalant substance is provided into the test chamber, wherein performing the inhalation test comprises a) collecting during the course of the inhalation test respiration-related measurements for respiration cycles of the test subject using the sensing device applied directly to the test subject, b) applying the calibration formula to the respiration-related measurements as they are collected during the inhalation test to determine during the course of the inhalation test a running measure of cumulative respiration volume for the test subject, and c) storing the running measure in computer storage memory.

In various implementations, the method and corresponding apparatus may include one or more of the following. The sensing device applied directly to the test subject may be a monitoring system comprising electrodes positioned to make impedance measurements across or around a portion of the lungs of the test subject, or more generally, impedance measurements that are sensitive to lung volume changes or lung changes. In the latter cases it is noted that respiration may be detected by electrodes that are arranged away from the lung, instead of across or around the lungs, but the current still traverses the body tissues that change in proportion to the lung volume.

In addition, the sensing device used in the method and applied directly to the test subject may be implanted within the test subject, and in this case may include electrodes positioned to make impedance measurements across or around a portion of the lungs of the test subject, and a wireless transmitter to transmit the collected respiration-related measurements to external processing equipment. Alternatively, the sensing device applied directly to the test subject may be worn by the test subject, and in this case may include electrodes positioned on the test subject to make impedance measurements across or around a portion of the lungs of the test subject, and a wireless transmitter to transmit the collected respiration-related measurements to external processing equipment. A sensing device worn by the test subject may also include elastic bands positioned on the test subject to make expansion measurements across a portion of the lungs or abdomen of the test subject, and a wireless transmitter to transmit the collected respiration-related measurements to external processing equipment.

In the method, the respiration volume measurements collected during the calibration procedure may be made using a pneumotachograph or other acceptable spirometer. The calculation of the calibration formula may include performing a best-fit process of the collected measurements forming a relationship between the collected respiration-related measurements and the collected respiration volume measurements, wherein a formula for the relationship is the calibration formula. The performing of the inhalation test further comprises calculating for each respiration cycle a respiration volume measure for that cycle using the respiration-related measurement for that cycle and applying the calibration formula to that respiration-related measurement, and summing calculated respiration volume measurements for each cycle to provide the running measure of cumulative respiration volume for the test subject.

The method may further include determining during the course of the inhalation test a running measure of cumulative dosage of inhalant substance inspired by the test subject. In such a case, the method may further include calculating for each respiration cycle a dosage inspired for that cycle using a respiration volume measurement for that cycle, and summing calculated dosage measurements for each cycle to provide the running measure of the cumulative dosage inspired.

In the method, the performing of the inhalation test may further include comparing the running measure of cumulative respiration volume to a selected threshold value, and triggering a predefined action to occur if the running measure of cumulative respiration volume reaches the selected threshold value. The predefined action may include at least one of discontinuing providing the inhalant substance into the test chamber, changing the concentration of the inhalant substance being provided into the test chamber, changing the volume of the inhalant substance being provided or the pressure of the exposure system into the test chamber, or changing the pressure in the test chamber. The predefined action, alternatively or additionally, may include at least one of providing an indication of the threshold having been reached, and marking a point in time at which the threshold is first reached. The method may further include monitoring a physiological attribute of the test subject, and correlating a specified state of the physiological attribute with the value of the running measure of the cumulative respiration volume at the time the specified state of the physiological attribute was detected.

In another aspect, there is provided a monitoring system for use during an inhalation test on a test subject. The monitoring system includes a processor device; a test chamber configured to at least partially confine the test subject; a sensing device adapted to be applied directly to the test subject for measuring respiration-related measurements; and a test chamber sensing device configured to sense atmospheric changes of a volume within the test chamber;

wherein the processing device further comprises: a calibration processing module programmed to a) receive respiration-related measurements for each of multiple respiration cycles taken from the test subject using the sensing device adapted to be applied directly to the test subject, b) receive separate corresponding respiration volume measurements for each of the multiple respiration cycles of the test subject determined by the test chamber sensing device configured to sense atmospheric changes of a volume within the test chamber, c) use the received respiration-related and respiration volume measurements to calculate a calibration formula that correlates respiration-related measurements received using the sensing device adapted to be applied directly to the test subject to respiration volume measurements, and d) store the calibration formula in memory of the monitoring system. The processor device also includes a test procedure processing module programmed to a) receive during the course of an inhalation test respiration-related measurements for respiration cycles of the test subject using the sensing device adapted to be applied directly to the test subject, b) applying the stored calibration formula to the respiration-related measurements as they are collected during the inhalation test to determine during the course of the inhalation test a running measure of cumulative respiration volume for the test subject, and c) storing the running measure in memory of the monitoring system, wherein the test procedure processing module is configured to perform the inhalation test on the test subject, and during the inhalation test the test subject is at least partially confined within the test chamber and an inhalant substance is provided into the test chamber.

In various implementations, the monitoring system may include one or more of the following components or features. The calibration processing module may be further programmed to perform a best-fit process of the received measurements forming a relationship between the received respiration-related measurements and the received respiration volume measurements, wherein a formula for the relationship is the stored calibration formula. The test procedure processing module may be further programmed to calculate for each respiration cycle a respiration volume measure for that cycle using the respiration-related measurement for that cycle and apply the stored calibration formula to that respiration-related measurement, and sum calculated respiration volume measurements for each cycle to provide the running measure of cumulative respiration volume for the test subject.

The test procedure processing module may be further programmed to determine during the course of an inhalation test a running measure of cumulative dosage of inhalant substance inspired by the test subject. In this case, the test procedure processing module may be further programmed to calculate for each respiration cycle a dosage inspired for that cycle using a respiration volume measurement for that cycle, and sum calculated dosage measurements for each cycle to provide the running measure of the cumulative dosage inspired.

The test procedure processing module may also be programmed to compare the running measure of cumulative respiration volume to a selected threshold value, and trigger a predefined action to occur if the running measure of cumulative respiration volume reaches the selected threshold value. The predefined action comprises at least one of discontinuing providing the inhalant substance into the test chamber, changing the concentration of the inhalant substance being provided into the test chamber, or changing pressure of the test chamber.

In another aspect, there is provided a method of performing an inhalation test on a subject during which inhalation test the test subject is at least partially confined within a test chamber and an inhalant substance is introduced into the test chamber. The method includes a) collecting during the course of the inhalation test respiration-related measurements for respiration cycles of the test subject using the sensing device applied directly to the test subject, b) timing inhalant concentration changes to a particular phase within a respiratory cycle, c) assessing a respiratory pattern of the test subject, and d) adjusting inhalant particle size based on the respiratory pattern.

In various implementations, the method may also include determining, from the respiratory pattern of the test subject, whether a particle size of the inhalant needs to be modified, and modifying the inhalant particle size in accordance with the determination. Also, the method may also include determining, from the position in time within the respiratory cycle of the test subject, the need to modify inhalant concentration, and modifying the inhalant concentration in accordance with the determination.

In another aspect, there is provided a monitoring system for use during an inhalation test on a test subject. The monitoring system includes means for receiving during the course of an inhalation test respiration-related measurements for respiration cycles of the test subject; means for determining a critical position in time within the respiratory cycle of the test subject; means for assessing respiratory patterns of the test subject; and means for modifying the size and/or concentration of the inhalant delivered to the test subject.

In various implementations of the system, the need to modify inhalant particle size may be determined by the respiratory pattern of the test subject. In addition, the need to modify inhalant concentration is determined from a position in time within the respiratory cycle of the test subject.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a diagram of an example inhalation system.

FIG. 2 is a diagram of an example externally worn animal respiratory monitoring system shown on a canine animal.

FIG. 3 is a diagram of an example implantable animal respiratory monitoring system shown implanted in a rat.

FIG. 4 is a graph of two charts that illustrate, at bottom, example impedance data obtained from a respiratory monitoring system and, above, respiration volume data derived from a standard respiratory flow method (pneumotach).

FIG. 5 is a graph that shows the relationship of impedance data and data taken by a pneumotach, so as to illustrate an example method of calibrating prior to an inhalation drug test.

FIG. 6 is a flow diagram of an example process for performing an inhalation drug test.

FIG. 7 is a flow diagram of an example process for the calibration process identified in FIG. 6.

FIG. 8 is a flow diagram of an example process for the inhalation testing procedure identified in FIG. 6.

FIG. 9 is a flow diagram of an example process for changing the particle size of an inhalant to target delivery of the inhalant to a specific target site.

FIG. 10 is a flow diagram of an example process adjusting inhalant concentration during the inspiratory phase of the respiratory cycle.

FIG. 11 is a block diagram of an example external receiving and a processing circuitry that may be used in executing the disclosed calibration and testing processes.

FIG. 12 a block diagram of computing devices that may be used to implement the systems and methods described in this document Like reference symbols in the various drawings indicate like elements.

DETAILED DESCRIPTION

FIG. 1 illustrates an example drug testing system 100. The inhalation system 100 may be used for example to test the effects of an inhalant drug on a test subject 120 that is inside a test chamber 105 of the system 100, wherein the inhalant drug is introduced into the test chamber 105 to be breathed in by the test subject 120. Generally speaking, the system 100 enables, during a test, substantially real-time respiratory measurements of the test subject 120 using various techniques that obtain measurements of respiration directly from the test subject, including, but not limited to, respiratory inductance plethysmography (RIP), impedance measurements, elastomeric plethysmography, and other chest and/or abdominal expansion measurement techniques. These respiratory measurements taken directly from the test subject 120 may be for example transmitted for processing during the course of the test to a processing system, to determine a cumulative volume of inhalant inspired by the test subject 120, and from that, a cumulative amount of substance (or dose) inhaled by the test subject 120.

By using respiratory measurement techniques that take measurements directly from the test subject 120 during the course of a test or study, it is possible to avoid the use of measurement techniques that endeavor to make atmospheric measurements of the atmosphere within the test chamber 105 including the inhalant in that atmosphere. As such, it is possible to avoid disadvantages of using such atmospheric measurement techniques, for example, time-consuming or expensive sterilization procedures required to reuse the system 100 for the next test, and/or having to perform difficult cleaning operations following a test to clean filters for example that are interposed between the atmosphere of the test chamber 105 and the atmospheric measurement system.

In addition, it is desirable to perform a calibration procedure before the disclosed inhalant exposure. A calibration provides the correlation needed to translate chest and/or abdominal wall expansion measurements, made during the test, into lung volume measurements from the test subject 120. As such, in a calibration procedure, the atmospheric measurement system may be used to obtain a respiratory volume measurement (for example, a volume measurement for each breath of the test subject 120), while at the same time chest and/or abdominal wall expansion measurements are taken directly from the test subject using the same measurement technique that will later be used during dosing. Because no inhalant drug need be introduced into the test chamber during the calibration process, the disadvantages of using the atmospheric measurement system discussed previously are not present.

The example system 100 includes the test chamber 105, a reference chamber 110, and a pneumotachograph 115. The test chamber 105 encloses an enclosed volume that can contain the test subject 120 such as a mouse, rat, rabbit, dog, or other animal, and into which enclosed volume an inhalant (e.g., drug, toxin, bacteria, virus, medication) may be introduced. As the test subject 120 breathes, the volumes of air inhaled and exhaled by the test subject 120 cause an air pressure and/or flow difference between the test chamber 105 and the reference chamber 110, and this difference is detected by the pneumotachograph 115. The pneumotachograph 115 outputs an analog signal, such as an electrical voltage or current that varies in response to the detected differential. The analog signal transmitted by the pneumotachograph 115 is received by an analog to digital (A/D) converter 125 which transmits a digital signal representative of the analog signal. The digital signal transmitted by the A/D converter 125 is received by an automated inhalation exposure system 130. The automated inhalation exposure system 130 interprets the digital signal that represents the air pressure and/or flow changes caused when the test subject 120 breathes to determine the volumes of air inspired by the test subject 120.

The system 100 also includes an external receiving and processing component 135. The receiving and processing component 135 is communicably coupled (for example, wirelessly) to one or more physiological sensors (not shown) attached to or implanted in the test subject 120, as well as being communicably coupled (for example, by wired connection) to the automated inhalation exposure system 130. In various implementations, the physiological sensors, which can be implantable or external, may be used to obtain substantially real-time measurements related to respiration (e.g., impedance, RIP). The receiving and processing component 135 receives the measurements collected by the physiological sensors and transmits the measurements to the automated inhalation exposure system 130 (for example, a computing system with programmed circuitry to execute the calibration and testing processes described in more detail later in this document), thus enabling the automated inhalation exposure system 130 to measure the physiological changes that may occur as the test subject 120 breathes. In the illustrated example, the receiving and processing component 135 is communicably coupled to the physiological sensors by a wireless link 140, but in some implementations the link may be made using wires, light (e.g., fiber optics, infrared communications), or sound (e.g., ultrasonic transceivers). In addition, although in the FIG. 1 example components 135 and 130 are shown as separate components, they may be a single component. In addition, in some embodiments the functions of these two components 135 and 130 may be performed in multiple components of a networked computing system or a single combined system (130:125,135).

Figure 2:
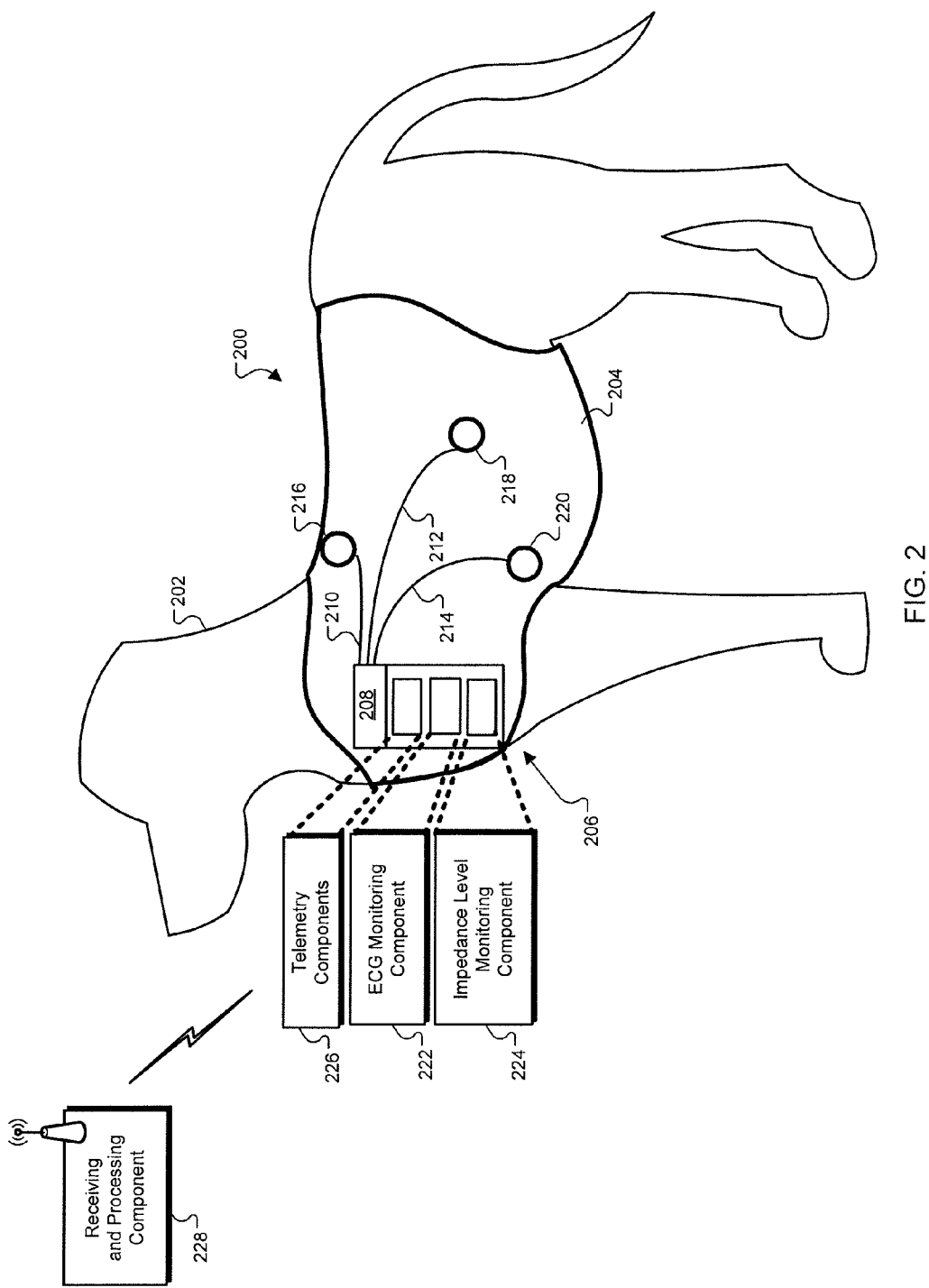

An implementation of the physiological sensors as an external system may consist of external electrodes or respiratory bands alone or in combination with a wearable structure such as a jacket. The external electrodes may be positioned, for example, to take impedance measurements through an internal path of the animal that includes the animal's lungs or correlates to changes in lung volume. The electrodes can be tethered to a processing and control device via electrical signal conduits. These conduits and the processing and control device may also be housed within the wearable structure. An example of such an external system is shown in an example of a canine model FIG. 2 and is discussed in more detail below. It will be appreciated that although FIG. 2 shows the externally worn monitoring apparatus in the context of a canine model, externally worn monitoring apparatus may be used in other animal models as well.

An implementation of the physiological sensors as an implantable device is an alternative that may be used in lieu of externally worn or applied sensors. An implantable monitoring device is shown in the example of a rat model in FIG. 3 and is discussed in more detail below. The components of the implantable device are similar to those of the externally worn device, and generally include electrodes, processing circuitry, and telemetry circuitry and components. The implantable electrodes may be positioned so that impedance measurements may be taken across an internal volume of the test subject that includes a portion of the animal's lungs or a path that correlates to changes in lung volume.

Figure 5:
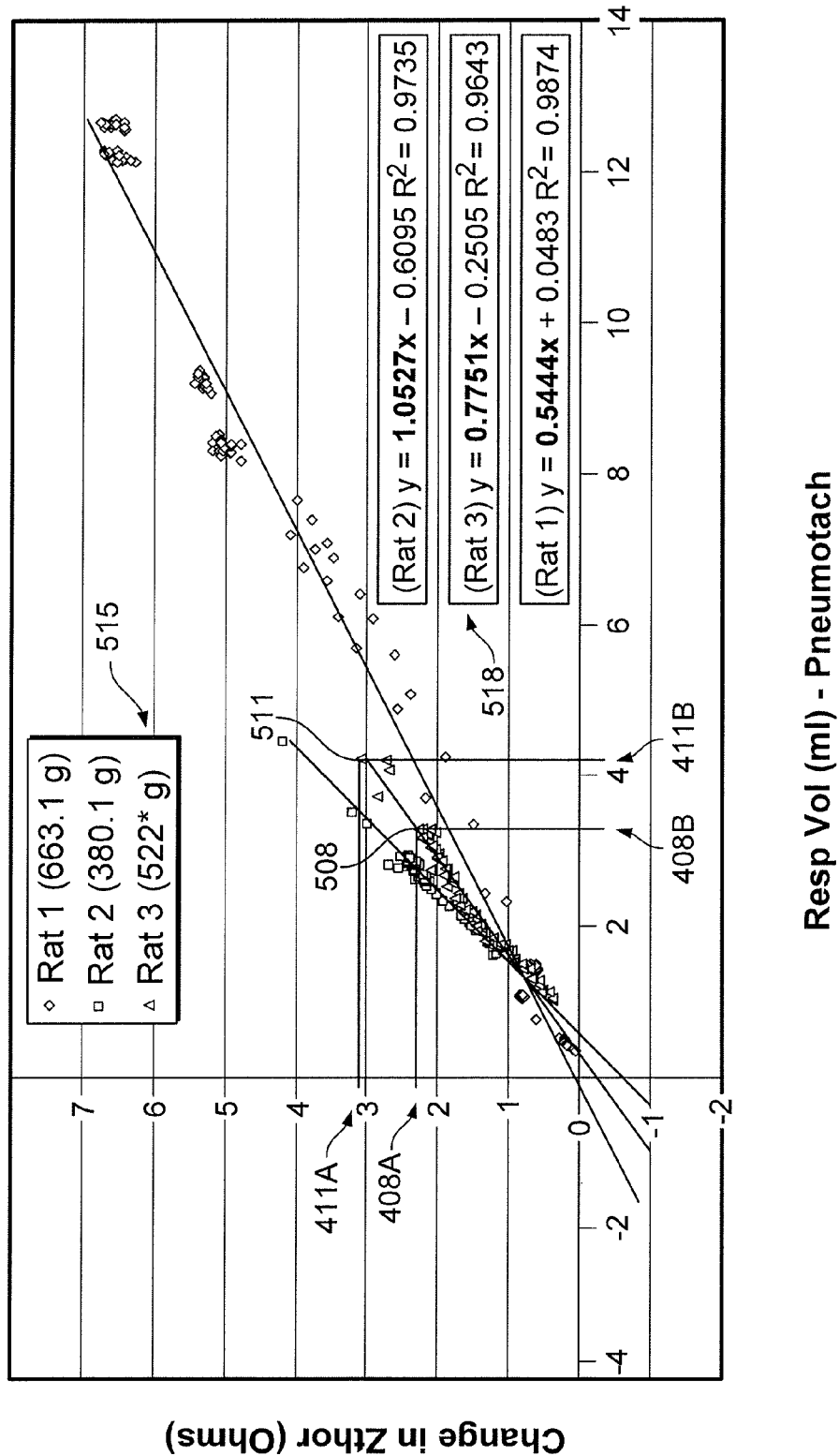

Generally speaking, a calibration process may be performed for the chambers 105-110 (FIG. 1) and the test subject 120 to determine a correlation between measured respiratory volumes and measured physiological parameters. For example, measurements taken by the physiological sensors alone may provide information about how and when the test subject 120 breathes, but without an external reference that correlates this data to respiratory volume it may not be possible to determine, solely from the physiological sensor data (for example, impedance measurements across the lungs and more specifically, the change of impedance from a time before the animal has taken in a breath to a time when the animal has taken in a breath), the volumes of air inspired by the animal for example during a breath. By comparing the measurements taken by the pneumotachograph 115 (a type of atmospheric sensor for the chamber) and the physiological sensors directly applied to the test subject, a correlation between the physiological signals (e.g., respiratory impedances, RIP) and the pneumotachograph signals (e.g., respiratory volumes) for the test subject 120 can be determined. This correlation can then be used to determine a measure of the volume of air inspired from the physiological sensors without requiring the use of the pneumotachograph 115 during the actual time when an inhalant is introduced into the test chamber. Example correlations between the physiological signals taken directly from the animal and pneumotachograph measurements are shown in FIG. 5, and an example calibration process is discussed further in connection with the description below of FIG. 7.

Once the test subject 120 has been calibrated in testing system 100, the respiratory volumes of test subject 120 can be used to measure substantially real-time respiratory parameters of interest such as breathing rate and volume without further use of the pneumotachograph 115 during the actual test. As such, the downside of prior methods of the screens becoming clogged or contaminated by the inhalant introduced into the test chamber 105 while the pneumotachograph 115 is taking measurements need not be present. By way of background for example, an inhalant such as a drug, toxin, medication, or other substance may be provided by an inhalant supply 145. The inhalant from the inhalant supply 145 is provided to a showerhead 150 which aerosolizes or otherwise causes the inhalant to become airborne within the test chamber 105, thereby allowing the test subject to breathe in the inhalant from the ambient air within the test chamber 105.

During the actual test, as the test subject 120 breathes, a respiratory volume for each breath may be determined by the automated inhalation exposure system 130. In some implementations, the volume measurements may be multiplied by one or more factors such as an inhalant concentration or a term that accounts for the amount of inhalant absorbed by the test subject 120 (e.g., coefficient of absorption). The product of the resultant multiplication can be summed over time to produce a cumulative dose measurement of the inhalant.

In some implementations, the automated inhalation exposure system 130 may be programmed to respond to the measured physiological signals, cumulative dosage measurement information, or other measured or calculated data. For example, once the cumulative dosage measurement equals or exceeds a threshold dosage that may be selected by a user or determined in some other manner, the automated inhalation exposure system 130 may stop the flow of inhalant into the test chamber 105 by signaling a remotely controllable valve 155 to close. This may be useful, for example, if it is desired that the test subject take in no more than a predefined amount of drug or other substance in the inhalant. In another example, the automated inhalation exposure system 130 may regulate (or document) the amount of inhalant provided to the test chamber 105 in response physiological changes sensed within the test subject 120 (for example, by internal pressure sensors that may be part of the implanted device and that may, for example, continuously monitor the blood pressure of the test subject). For example, it may be that it is desired to determine the dosage given at the time a specific reaction took place in the test subject. In yet another example, the automated inhalation exposure system 130 may trigger an alarm to alert a human operator (e.g., lab technician), for example when a predetermined total dosage has been delivered to the test subject 120. This may be useful, for example, should it be desired to make a visual observation of the test subject at a time when a specified amount of the inhalant has been inspired by the test subject.

Figure 3:
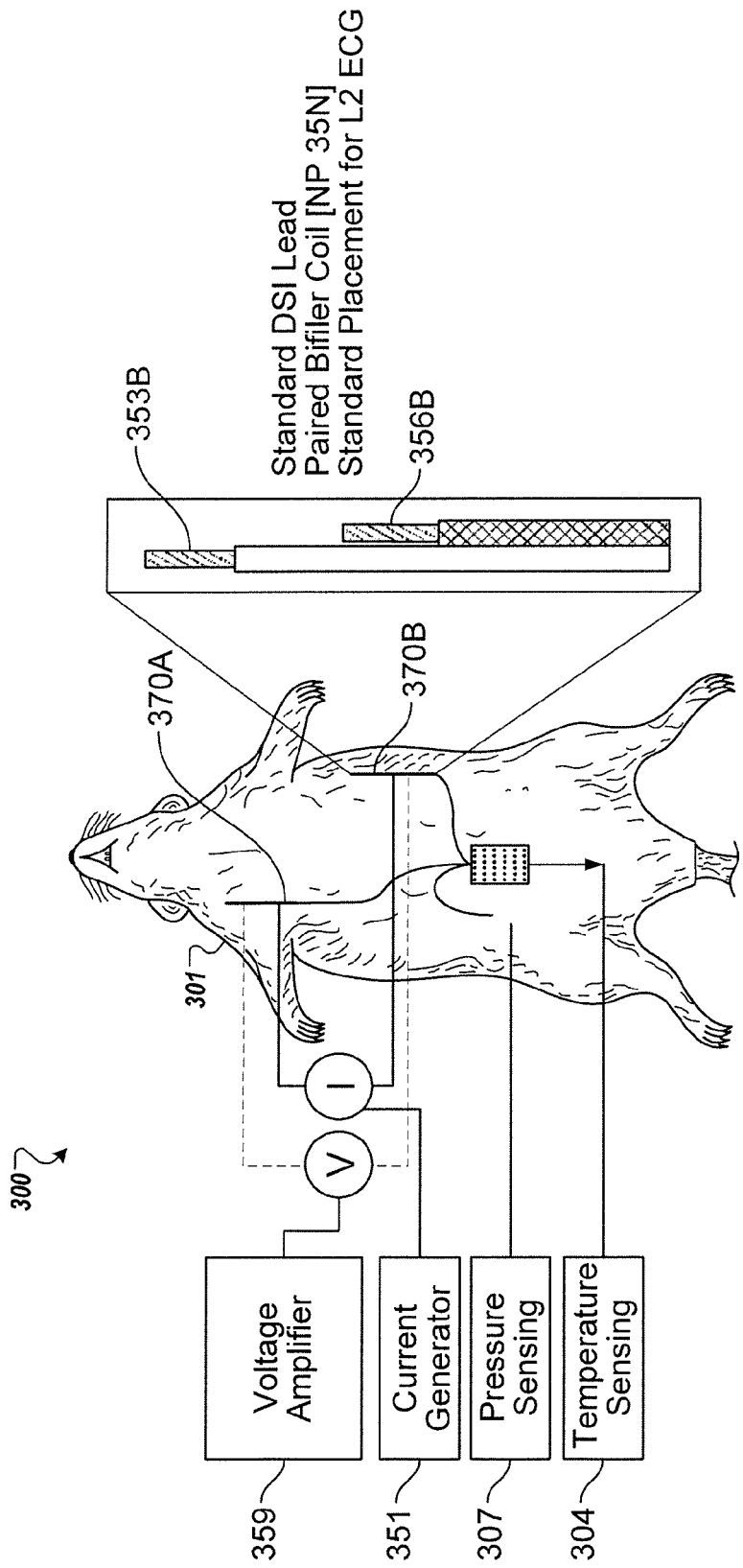

During preclinical testing of pharmaceutical compounds on animal subjects such as the test subject 120 for example, various physiological parameters of the animal subjects can be monitored using an animal monitoring system such as the system 200 shown in FIG. 2 or the system 300 shown in FIG. 3. In some implementations, the animal monitoring system 200 or 300 can be the physiologic sensors described in FIG. 1.

In particular, systems 200 and 300 can monitor physiological parameters of the animal while the animal is ambulatory and free from tethered wiring, tubing, or other encumbering equipment. In some implementations, animal monitoring systems 200 and 300 can be used to acquire and analyze both ECG data and time varying impedance values in the animal's body. The ECG data and impedance level data can be acquired non-invasively using two or more electrode devices placed on the skin surface of the animal subject. The electrodes can be used to sense ECG signals and impedance levels of the animal. More specifically, time-varying thoracic impedance values, time-varying abdominal impedance values, and ECG values can be obtained from the electrode devices concurrently, successively, or in an overlapping manner. In some implementations, further analysis can be performed on the obtained data to ascertain values for respiratory volume, respiratory rate, inspiratory time or interval and flow, and expiratory time or interval and flow. In other implementations, other sensors may be included in the animal monitoring system 200. For example, monitoring system 200 may include an implantable pressure sensor that wirelessly transmits data to one of the telemetry components of processing device 206. In addition, as shown with the system 300, the monitoring system 300 may include one or more additional implantable sensors including but not limited to a pressure sensor for continuously monitoring an internal pressure of the test subject, for example, blood pressure, a temperature sensor for monitoring body temperature of the test subject, a blood gas sensor for monitoring oxygen and carbon dioxide levels in the test subject and a glucose sensor for monitoring blood sugar of the test subject.

FIG. 2 is a diagram of the example external ambulatory animal monitoring system 200 shown fitted on a canine laboratory animal 202. In one implementation, the system 200 includes a wearable structure, such as a jacket 204, that is constructed to be worn about the torso or body of the canine 202 to facilitate monitoring functions. For example, the jacket 204 is shown placed on the canine 202 in such a fashion that the jacket 204 protects or shields electrode(s) on the animal while not restricting ambulatory movement of the canine by way of tethering the animal to stationary equipment. Although FIG. 2 illustrates the animal monitoring system 200 placed on a canine animal, other animal species can be fitted with the system 200 for monitoring purposes, such as mice or rats, rabbits and other test subjects.

The depicted example jacket 204 includes a processing and control device 206 that may be adapted to be worn with, attached to, or otherwise fastened to the jacket 204. For example, the processing and control device 206 may be placed within a pocket or sleeve on the jacket 204 or alternatively may be affixed to the jacket, such as with hook-and-loop fastener, tape, or any other fastener. The processing and control device 206 can, for example, be used to inject current to the canine 202 via surface electrodes and measure signals received at one or more of the surface electrodes. Generally, one example process of taking an impedance measurement across a test subject's lungs involves first injecting a current between two electrodes positioned such that current flows through or around a volume of the lungs, followed by a measurement process wherein a resulting voltage is measured between two electrodes also positioned such that the measurement traverses a portion of or around the lungs. In some electrode configurations, the electrodes that inject current between them may be separate from the detection electrodes. In other configuration, there may be a common electrode. As such, three-electrode configurations may be used, in which one of the three electrodes is used both for current injection and voltage measurement. In addition, four electrode configurations may alternatively be used, in which two electrodes are used for current injection and two different electrodes are used for measurement. Again, the electrodes are positioned such that measurements of impedance may be taken though an internal volume of the test subject that includes a portion of the test subject's lungs.

The processing and control device 206 here includes a wiring system 208 that can include any number of electrical signal conduits for use in the monitoring. For example, the conduit(s) can allow disposable surface electrodes to be removably connected to the device 206. The illustrated system 200 here includes three electrical wires 210, 212, and 214 which are detachably connected to the wiring system 208. In one example, the electrical wires 210, 212, and 214 may be combined in an electrical harness constructed for attachment to the wiring system 208. The wire harness (210-214) and surface electrodes (216-218) can be attached within the wiring system 208 to electrical signal conduits. The connection to the electrical signal conduits may be provided by a single connector or separate connectors for each wire. Any kind of electrical connector can be used, such as a plug. In some implementations, the electrical wires 210-214 can be fixedly attached to wiring system 208 and disposable electrodes can connect at the ends of the wires 210-214.

In some implementations, each wire 210, 212, and 214 may be connectable to a different surface electrode component. As shown in FIG. 2, the wires 210, 212, and 214 are connected, respectively, to surface electrode components 216, 218, and 220. In some implementations, the electrical wires 210, 212, and 214 and the surface electrode components 216, 218, and 220 can be permanently attached to each other, respectively, and may therefore provide pluggable component(s) to wiring system 208.

The processing and control device 206 in this implementation includes an ECG monitoring component 222, an impedance level (IL) monitoring component 224, and a telemetry component 226. In one example implementation, the components 222, 224, and 226 can be included in one packaged device that can be held by the jacket 204. In some implementations, the ECG monitoring component 222 and the IL monitoring component 224 may be placed in one area of the jacket 204, while the telemetry component 226 can be placed elsewhere to, for example, facilitate wireless access to the jacket 204 and/or decrease interference noise that may be caused when operating components 222 and 224 in the vicinity of a wireless transceiver. The ECG monitoring component 222 and the IL monitoring component 224 can be provided as separate components or integrated into a common component.

In general, the ECG monitoring component 222 can generate data indicative of an ECG signal over time by measuring the ECG signal of the animal using two or more surface electrode components connected to respective electrical signal conduits. For example, the ECG monitoring component 222 can measure the electrical potential between the surface electrode 216 and the surface electrode 220 to provide a differential bio-potential signal. In some implementations, signals on both electrodes 216 and 220 may be measured at some frequency to determine the ECG signal over time.

The IL monitoring component 224 generates data indicative of electrical impedance levels in the animal 202 over time. In some implementations, the IL monitoring component 224 can inject a current between two or more surface electrodes connected to a number of electrical signal conduits. For example, the IL monitoring component 224 can inject current between surface electrodes 216 and 218, between surface electrodes 218 and 220, or between surface electrodes 216 and 220 shown in FIG. 2. In some implementations, ECG and impedance can be measured using two surface electrodes, such as the surface electrodes 216 and 218. In other implementations six or even more surface electrodes may be employed. Accordingly, fewer or more surface electrodes than in the present example can be used to monitor physiological parameters, such as ECG and impedance levels in an animal.

The IL monitoring component 224 can measure a resulting voltage level that occurs between surface electrode components as a result of the current being injected. For example, if the IL monitoring component 224 injects current between surface electrodes 216 and 218, any of the surface electrodes, such as the surface electrode 218, can measure the resulting voltage.

In some implementations, various parameters in components 222 and 224 may be adjustable or programmable, either automatically (e.g., using signals transmitted from a receiving and processing component 228) or manually (e.g., accessing the device 222 or 224 in the jacket 204 and entering parameters). In one example, the gain for individual electrode sensors may be adjustable (e.g., manually, or automatically) to facilitate a high signal-to-noise ratio in a variety of operating environments. In some implementations, frequency and current amplitude are both adjustable to maximize the signal-to-noise ratio while minimizing power consumption.

The telemetry component 226 can be adapted to be worn with the jacket 204 for wirelessly communicating generated ECG data and/or impedance level and/or pressure data. For example, the telemetry component 226 can send data to the receiving and processing component 228 located elsewhere, such as in a laboratory or a medical facility where the animal is being monitored. In some implementations, the receiving and processing component 228 may be the receiving and processing component 135 and/or the computing system 130 of FIG. 1. In some implementations, the ECG data and impedance level data can be sent to the receiving and processing component 228 substantially in real time, for example, data may be transmitted essentially continuously as the data are collected, at predefined intervals such as a few seconds between transmissions, or in some cases even longer periods of time between successive transmissions.

The receiving and processing component 228 (or components 135 and/or 130 of FIG. 1) may receive ECG data, impedance level data, and other physiological parameters sensed in the canine animal 202 and further process the data. The receiving and processing component 228 here includes a wireless receiver that receives generated data wirelessly from the processing and control device 206. The receiving and processing component 228 can convert detected voltages into an impedance (e.g., by dividing the magnitude of the detected voltage by the magnitude of the current signal). In some implementations, the receiving and processing component 228 may receive raw voltage data from the animal monitoring system 200, and the raw data could be appropriately filtered and processed. For example, the measured voltage (e.g., voltage sensed by surface electrodes 216, 218, and/or 220) could be factored (divided by) a magnitude of an applied current (e.g., the current applied by the impedance level monitoring component 224) to determine instantaneous impedance values. In some implementations, the voltage measures may be used directly, as surrogate measures of impedance.

In some implementations, the animal monitoring system 200 can use one or more surface electrodes 216, 218, or 220 connected to corresponding conduits 210, 212, and 218 to measure and/or sample the ECG signal while additionally measuring the electrical impedance levels. In some implementations, the ECG signals are captured at substantially the same time that impedance values are obtained (e.g., signals on the appropriate electrodes may be sampled at some frequency, and the samples may alternate between sampling impedance information (e.g., voltage induced by the above-described current injection) and sampling ECG information (e.g., each sample or based on some other pattern, such as one impedance sample for every five ECG samples). In such implementations, the ECG (or other bio-potential information) may be sampled in a manner that is synchronized with the injected current signal (e.g., such that the sample is made when the IL monitoring component 224 is not actively providing current to the animal tissue, such as the off portion of a pulsed current signal). In other implementations, the electrical signal conduits (210-214) and/or the surface electrodes (216-220) may be used for either capturing ECG or other bio-potential information, or for capturing thoracic impedance information or abdominal impedance information, and the current injected into the electrodes may be remotely programmable or adjustable. Other configurations and measurements can be used. For example, all three surface electrodes 216, 218, and 220 in the triangular configuration shown in FIG. 2 could be employed to capture bio-potential information.

FIG. 3 is an illustration depicting how an example implantable, wireless respiratory monitoring device 300 may be implanted in a laboratory animal such as the test subject 120 of FIG. 1. In some implementations, the wireless respiratory monitoring device 300 may be the physiologic sensors described previously, for example in connection with FIG. 1. FIG. 3 is a diagram of the implantable monitoring device 300 implanted in a laboratory rat 301. For purposes of example, a tetrapolar lead (four lead) arrangement is depicted, and a temperature sensor 304 and a pressure sensor 307 are also shown to be included in the device and implanted in the laboratory rat 301. As such, this system is capable of obtaining various other physiological measures, beyond respiratory information, that may be useful in the testing process so as to allow the system to respond during the course of an inhalation test in manners described previously. In one implementation as shown, pairs of electrodes are physically disposed in a first lead wire 370A and a second lead wire 370B. In this example, a current signal is propagated from a first electrode on the first lead wire 370A to a second electrode 353B on the second lead wire 370B, and a resulting voltage difference is detected between a third electrode on the first lead wire 370A and a fourth electrode 356B on the second lead wire 370B. A current generator 351 and a voltage amplifier 359 are depicted outside of the laboratory rat 301 for illustration purposes and clarity, but the reader will appreciate, that the current generator 351, the voltage amplifier 359 and other components can be fully implanted in the laboratory rat 301.

Calibration of the respiratory component of thoracic impedance is now described with reference to FIGS. 4 and 5. In some implementations, thoracic impedance data for a particular test subject is calibrated based on a separate measurement of respiration parameters (e.g., respiratory volume) using equipment other than the physiologic sensors. In particular, a pneumotachograph may be employed, or some other kind of plethysmography chamber to obtain respiration data from a test subject. It may be that the test subject is calibrated in the same chamber in which the test is conducted, although that may not be necessary in all cases.

Figure 4:
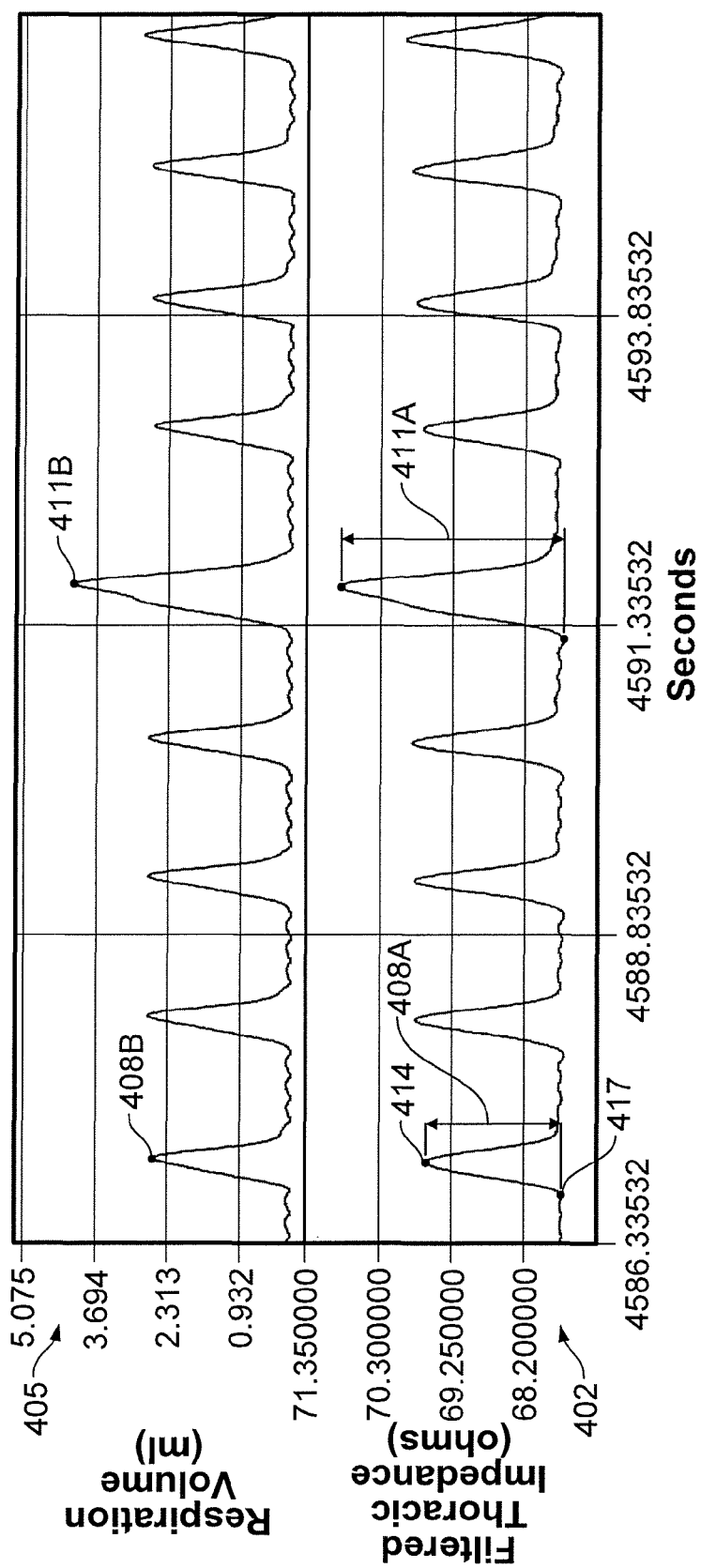

FIG. 4 illustrates example impedance data 402 corresponding to thoracic impedance obtained from physiologic sensors (shown in the bottom strip chart of FIG. 4), such as those described in FIGS. 1-3. FIG. 4 also illustrates, in the top strip chart, corresponding respiration data 405 (e.g., respiratory volume vs. time), which, in this example, was obtained from a test subject using an external device (a pneumotachograph) at the same time the thoracic impedance data 402 was obtained. Note that respiration volume is illustrated in FIG. 4, but respiration flow may have been obtained from the external device (test chamber). The reader will appreciate that in such a case, respiration volume can be obtained from respiration flow measures by a processing method that includes integrating the respiration flow.

The data 402 and 405 can be used to calibrate the thoracic impedance data 402 to actual respiratory volume, for example, to facilitate determination of respiratory volume and other parameters that can be derived from a respiratory volume vs. time plot when the test subject is not restrained by an external device such as a pneumotachograph. Calibrating the impedance data 402 can include calibrating a relationship between thoracic impedance and actual respiratory flow or volume—that is, determining constants of a equation that relates thoracic impedance to respiratory volume for a particular test subject.

Qualitatively, there may be in some cases a direct correlation between the measured change in thoracic impedance (that is, the respiratory component of thoracic impedance, which is implied in the discussion that follows) during a respiration cycle (single breath cycle) and the respiratory volume associated with that respiration cycle. FIG. 4 graphically depicts these values as follows: a change in impedance 408A for a first respiratory cycle corresponds to measured respiratory volume 408B (peak respiration volume); similarly, a change in impedance 411A for a second respiratory cycle corresponds to a measured respiratory volume 411B. In some implementations, an overall change in thoracic impedance can be determined by identifying a maximum thoracic impedance for a given respiration cycle (e.g., the maximum thoracic impedance 414 in the first respiration cycle) and subtracting from it a minimum thoracic impedance for the same respiration cycle (e.g., the minimum thoracic impedance 417 in the first respiration cycle). By identifying a number of changes in thoracic impedance and corresponding measured respiratory volumes, constants in the transfer function or correlation equation can be identified, and that equation with the identified constants can be employed with other thoracic impedance data to calculate a corresponding respiratory volume.

Additional details related to identifying (solving for) the constants in the transfer function or correlation equation are described with reference to FIG. 5. FIG. 5 illustrates a plot of various data points that represent corresponding pairs, where each data pair includes a change in thoracic impedance and a corresponding respiration volume. Respiration volume is plotted along the x-axis, and change in thoracic impedance is plotted along the y-axis. With reference to FIGS. 4 and 5, a data point 508 corresponds to the change in thoracic impedance 408A and the corresponding respiration volume 408B; a data point 511 corresponds to the change in thoracic impedance 411A and the corresponding respiration volume 411B. For purposes of example, many other data points are plotted, both for the same test subject 515 ("Rat 3") and for two other test subjects ("Rat 1" and "Rat 2").

By analyzing various data points for a particular test subject, a linear equation can be fit to the data (e.g., using a linear regression method) in order to determine a slope and offset for the equation. In the example shown in FIG. 5, the equation 518 for the test subject 515 has been determined to be:

$$y(\Delta \text{ohms}) = 0.7751 (\text{ohms/ml}) * x(\text{ml}) - 0.2505 (\text{ohms})$$

That is, change in thoracic impedance, in ohms, for test subject 515, is substantially equal to 0.7751 times the respiratory volume, in mL, minus 0.2505 ohms. The reader will appreciate that this equation can be rearranged to calculate respiratory volume, in mL, based on a corresponding change in thoracic impedance (e.g., as determined by the physiologic sensors). In particular:

$$x(\text{ml}) = \frac{y(\Delta \text{ohms}) + 0.2505(\text{ohms})}{0.7751(\text{ohms/ml})}$$

Data for other test subjects is also shown in FIG. 5. As shown, the slope of change-in-impedance/respiratory volume decreases based on the mass of the test subject. Accordingly, without higher-order calculations, the calibration relationship for a particular test subject may only be accurate for a period of time during which the mass of the test subject remains relatively constant. In some implementations, certain test subjects within a particular species may have a uniform enough impedance change/respiratory volume/mass relationship that an equation can be solved relating all three parameters. For example, thoracic impedance and/or respiration volume data may be normalized based on animal mass, and a linear regression technique may be applied to normalized data taken from a large enough sample of homogenous test subjects (e.g., the same or similar species, same general age, same general condition of health, etc.) to determine a unified equation relating respiratory volume to both change in thoracic impedance and mass of the test subject. In other implementations, the calibration process described with reference to FIGS. 4 and 5 is an acute calibration process for use with a single test subject and may need to be periodically repeated.

To characterize how well each linear equation describes the relationship between actual change-in-thoracic-impedance values and corresponding respiratory-volume values for a given test subject, linear regression of the data depicted in FIG. 5 has been performed for each test subject, and the $R^2$ value is shown. For the test subject 515 ("Rat 3"), the $R^2$ value is shown to be 0.9643—indicating a very good fit between the data and the above-described corresponding linear equation. Linear equations and corresponding $R^2$ values for other test subjects ("Rat 1" and "Rat 2") are also shown.

The data points are plotted to illustrate graphically the nearly linear relationship between change in impedance and corresponding respiratory volume. The reader will appreciate, however, that the relationship between change in thoracic impedance and corresponding respiratory volume can be determined without actually plotting the data. For example, in many implementations, the relationship is calibrated (that is, the constants in the equation are determined), by numerically analyzing various data points from thoracic impedance data captured from the test subject.

FIG. 5 illustrates a process to fit a linear equation to impedance data. The principles described herein can also be applied to fit a non-linear equation to impedance data. Non-linear fitting may be advantageous in certain animals, or in animals having certain conditions. For example, non-linear fitting of data may be particular applicable to the development of disease models, particularly, for example disease models that track changes to the respiratory system of test subjects as a disease progresses. Other applications of non-linear fitting are contemplated.

Figure 6:
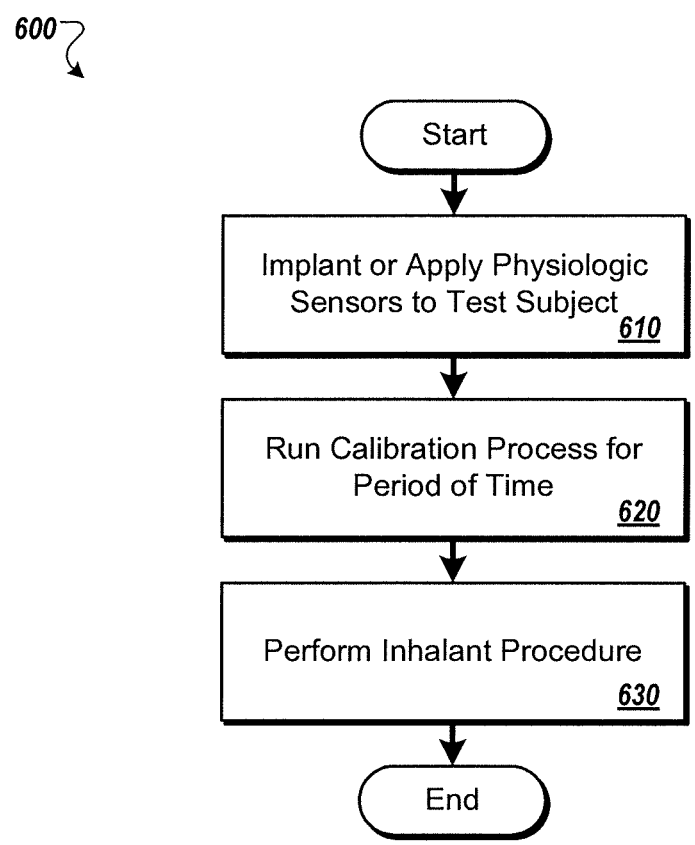

FIG. 6 is a flow diagram of an example process 600 for performing inhalant testing on a test subject wherein respiration volume is tracked during the test. In some implementations, the process 600 may be used by the system 100 of FIG. 1. The process 600 starts by implanting or applying physiologic sensors to a test subject in step 610. For example, a worn sensor system such as the system 200 of FIG. 2 may be placed on the canine laboratory animal 202, or the device 300 of FIG. 3 can be partly or entirely implanted in the laboratory rat 301.

Next, a calibration process 620 is then performed for a period of time during which the impedance change measures taken directly from the test subject are compared to a measure of respiratory volume, so as to create a calibration equation that will be used during the actual inhalation test that follows. Next, the actual inhalant testing procedure 630 is performed, in which the calibration equation is used, and a cumulative respiration volume measurement is made and continuously updated during the course of the test. As discussed previously, this cumulative respiration volume measurement may be used in a variety of ways during the test, for example, in monitoring the dose of inhalant substance (drug) that is taken in by the test subject. This may be used, for example, to determine when to stop putting further inhalant substance into the test chamber and/or to determine the amount of inhalant substance inhaled by the test subject when certain physiological responses occur in the test subject, to name a few examples of uses that may be made of this cumulative respiration volume information.

Figure 7:
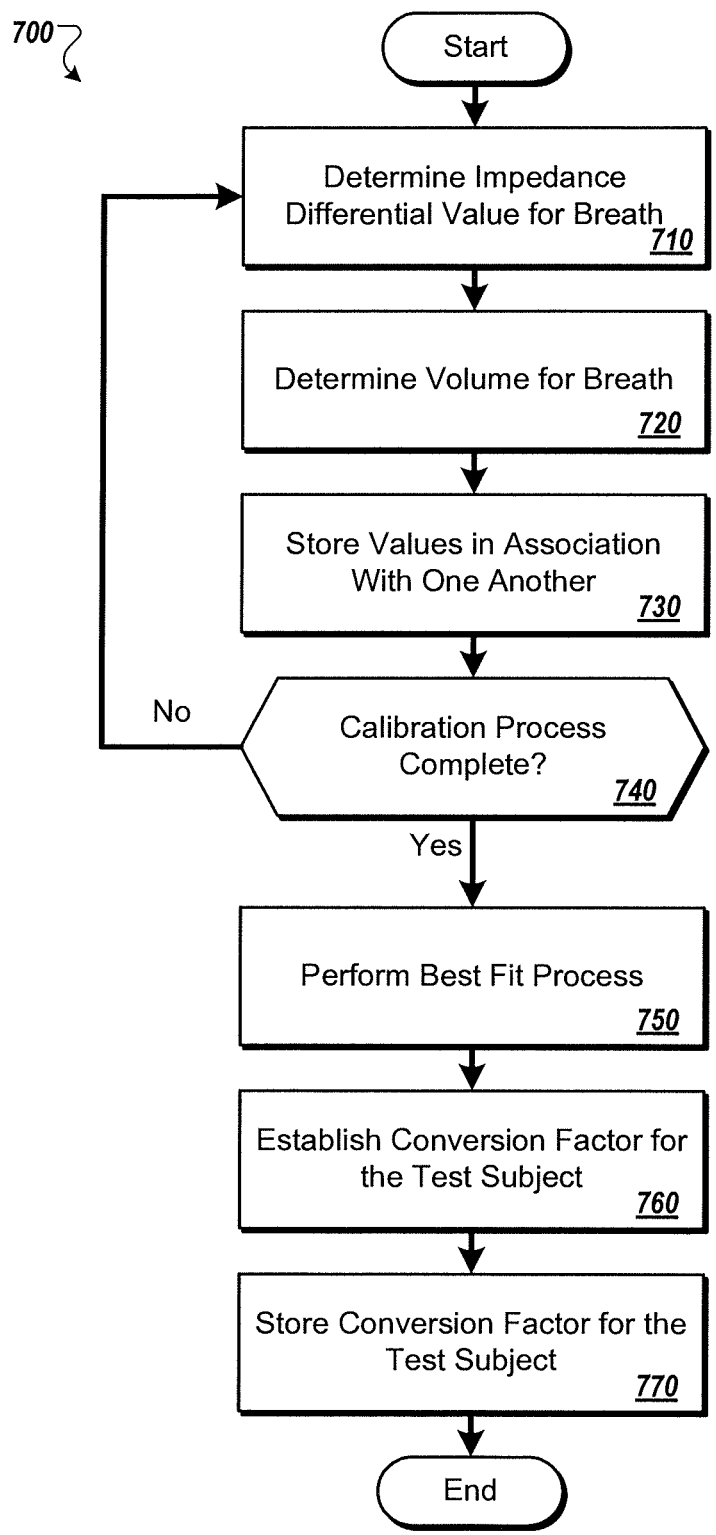

FIG. 7 is a flow diagram of an example calibration process 700 that may be used, for example, as the calibration process 620 used in the overall testing process of FIG. 6. The calibration process 700 starts by determining, in operation 710, an impedance differential value for a breath. For example, thoracic impedance for the test subject 120 may be monitored using physiologic sensors such as those included in association with the system 200 or the device 300. As the test subject breathes, the measured thoracic impedance may vary, as discussed previously for example in connection with FIG. 4. The determination of an impedance difference measure for a respiration cycle may be performed by the device implanted or externally worn by the test subject, and the impedance difference measure may be wirelessly transmitted to external equipment for further processing. Alternatively, collected impedance measures may be telemetered wirelessly from the test subject device to external equipment for processing, wherein an impedance difference measure for a respiration measure may be determined in the external equipment. In addition, a volume of the breath measure for each respiration cycle is also determined, at operation 720. For example, as the test subject breathes, a respiratory volume measurement as measured by a pneumotachograph may vary, also as discussed previously.

The values for the impedance (and/or impedance differences) and respiration volume measurements are transmitted to a common external processing device for example, and are stored 730 in computer storage memory in association with one another. Again, in the case of the impedance or impedance difference measures, this data may be transmitted wirelessly through the use of a telemetry system as previously described. In the case of the volume measurements, these may be for example transmitted by wired connection from the testing apparatus that makes the measurements, to the external processing device. These impedance (or impedance difference) and volume measures may be stored, for example, in memory of either component 135 or component 130 shown in FIG. 1. In some implementations, storing 730 the measurements in memory in association with one another can provide data that correlates impedance and volumetric measurements taken at substantially the same time. If the data collection part of the calibration process is determined, at operation 740, to be incomplete, then another impedance differential value is determined, at operation 710. For example, by storing, in operation 730, at least two associated impedance and volume values (but more typically many such measurement pairs), a linear relationship between the two measurements can be estimated. By storing, at operation 730, a greater number of associated values, a mathematical relationship can be estimated, for example, by calculating a best fit curve through the collection of measured values.

If the data collection portion of the calibration process is determined, in operation 740, to be complete (e.g., a sufficient number of associated values have been stored in memory, in operation 730), then a best fit process is performed, in operation 750. This operation may be performed by a programmed computing system in which a processor executes program code instructions stored in memory to perform various computer operations that calculate a calibration equation. In some implementations, the best fit process may be performed, in operation 750, using a linear regression processing technique such as that discussed previously in the description of FIG. 5. Once a best fit has been determined, the best fit information is used to establish, in operation 760, a conversion factor or equation for the test subject (or in other words, the calibration factor or equation). For example, the conversion factor or equation determined for one test subject may be different from that of another test subject. By determining the conversion factor for a given test subject, the drug test system can be calibrated to determine the various respiratory volumes that may be associated with the various thoracic impedances of the test subject. The conversion factor or equation for the test subject is then stored, in operation 770, in computer storage memory, for example, in memory of either component 130 or 135 in the FIG. 1 example system.

Figure 8:
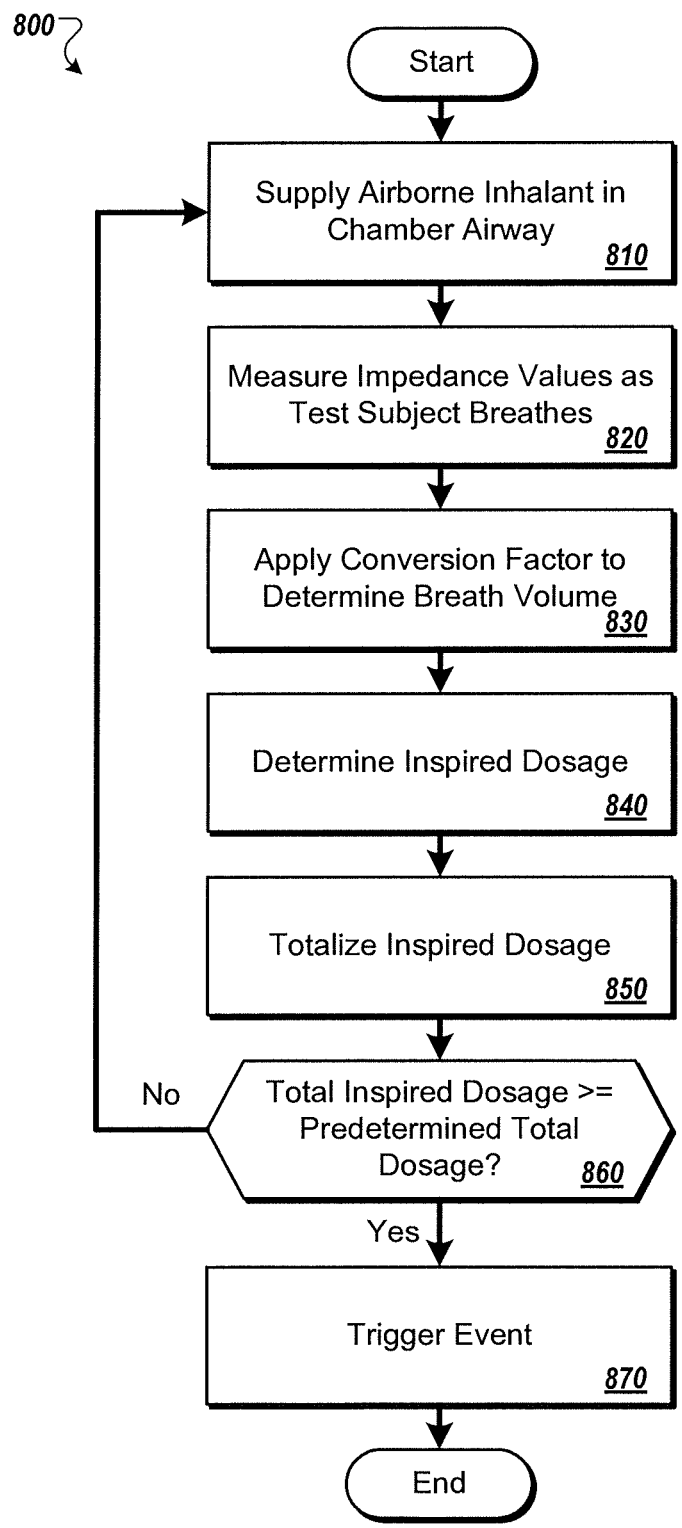
Figure 10:
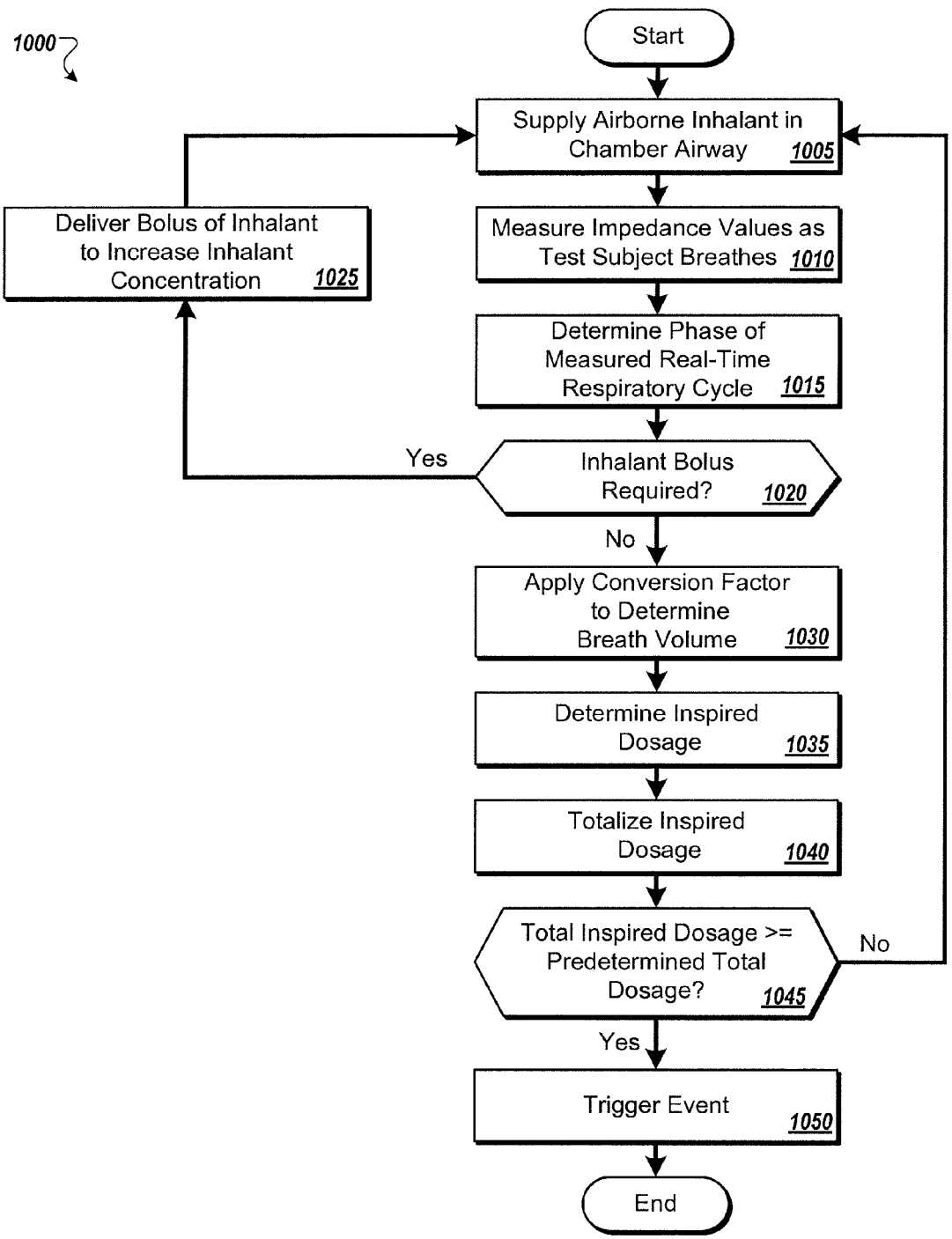
Figure 11:
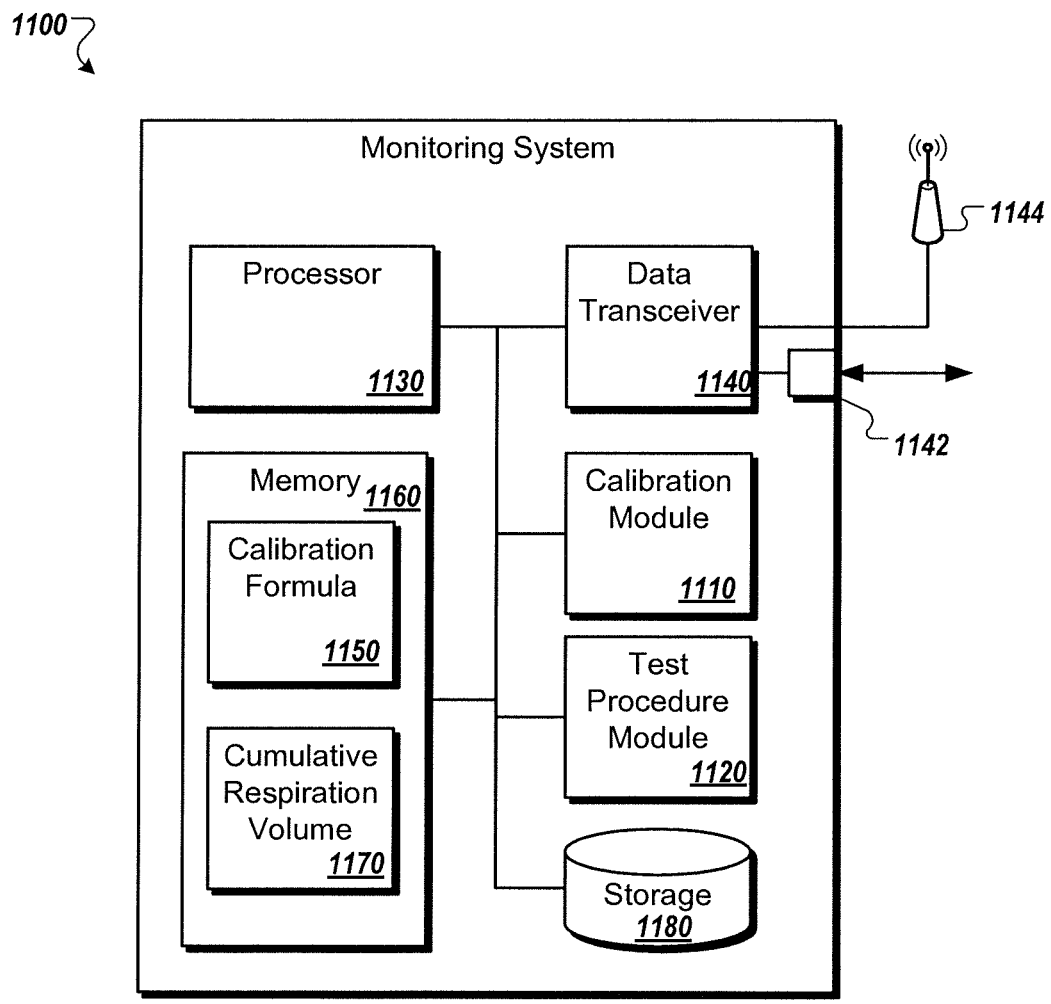

FIG. 8 is a flow diagram of an example testing process 800 that may be used for example as the inhalant testing procedure 630 included in the example overall testing process of FIG. 6. The testing process 800 begins by supplying, in 810 of the process, an airborne inhalant in a test chamber airway, with the test subject located within the test chamber. For example, the inhalant may be supplied into the test chamber by a nebulizer connected to an air supply for the test chamber. In another example, the airborne inhalant may be supplied into the test chamber through a showerhead, which aerosolizes the inhalant into the air enclosed within the test chamber.

Impedance values are then measured, at 820, by direct measurements from the test subject as the test subject breathes. These measurements are used to determine an impedance difference measure for each breath, and this difference measure may either be determined in the device implanted in or worn by the test subject, or in external equipment. The impedance measures or impedance difference measures, as the case may be, may be wirelessly transmitted from the device implanted or externally worn by the test subject to the external receiver and processing equipment, where impedance difference measures may be stored in memory of the external equipment. This external equipment, again, may be components 130 and 135 of the example system shown in FIG. 1. The impedance difference measure is then processed by the external equipment to provide an up-to-date (that is, real time) measure of cumulative respiratory volume and/or the dosage of inhalant substance taken in by the subject as the test proceeds. To do this, the external processing equipment performs a calculation in which the previously determined conversion factor or equation (e.g., the conversion factor stored in memory, in operation 770, during the calibration process 700) is then applied, at operation 830, to the impedance difference measure to determine a breath volume for the respiration cycle corresponding to the impedance difference measure. In other words, the volume taken in for a single breath may be determined from the impedance difference for that breath (from a point before the test subject begins to breathe in to a point at which the volume taken in the lungs is at its maximum for that cycle) and the stored calibration factor or equation.

An inspired dosage may then be calculated or determined, at step 840. This may be performed, for example, by applying various factors to the volume measure for the current respiration cycle, to determine an incremental dosage inspired for only that respiration cycle, and adding that to a running cumulative dosage value. The factors that are applied to the respiration volume for a particular respiration cycle may change over the course of a test, for example, because as the test progresses less dosage may be inspired for the same respiration volume. More specifically, the respiration volume for a respiration cycle, as determined in operation 840, may be multiplied by one or more factors including, but not limited to, inhalant concentration and a term that accounts for the amount of substance absorbed by the test subject (e.g., coefficient of absorption). In some implementations, dosimetry may be further refined by utilizing multiple absorption coefficients associated with various volumes of inspired inhalant. For example, changes in inhalant deposition in the respiratory tract, caused by varying ratios of inhalant in the lung to inhalant in dead spaces like the mouth and throat, can be reconciled.

The inspired dosage is then totaled in operation 850. For example, as the test subject breathes, the dosages determined, in operation 840, to have been inspired in each breath are summed over time to produce a cumulative dose measurement of the inhalant. If the total inspired dosage is determined, in operation 860, to be less than a predetermined total dosage, then the airborne inhalant continues to be supplied, at 810 in the process, in the chamber airway. For example, the object if the testing process may be to deliver 100 cc of a drug to the test subject via respiratory administration, however if less than 100 cc has been determined, in operation 860, to have been inspired by the test subject at the time of the determination in operation 860, the test may continue running.

Else, if the total inspired dosage is determined, in operation 860, to be equal to or greater than the predetermined total dosage, an event may be triggered, in operation 870. For example, once the predetermined dose has been reached or exceeded, the inhalant supply may be altered or halted, or a notification or alarm may be raised. In another example, once the predetermined dose has been reached or exceeded, the test process 800 may be repeated with a different inhalant, possibly with a different target dosage.

In addition to the operations described in the FIG. 8 flow chart, it will be appreciated that the respiration volume and dosage measures that are made during the course of the test may be stored in memory of the external equipment. In this manner, it is possible to determine the respiration and dosage when certain physiological conditions occur with the test subject. These conditions may be measured also by the devices implanted or worn by the test subject, or by visual indication. As such, an accurate measure of respiration volume and dosage may be made available for correlation to various responses found in the test procedure.

It should be noted that neither a pneumotachograph, nor any other form of measurement that requires sensors to be directly exposed to the air within the test chamber, are used during the testing process 800. In some implementations, the pneumotachograph or other such instrument used to take volumetric measurements for the calibration process 700 may be removed or otherwise isolated from the test chamber once the calibration process 700 is complete and prior to the commencement of the testing process 800. For example, the pneumotachograph or other volumetric sensors may be used during the calibration process 700 since no inhalant is supplied, and then removed prior to the testing process 800 when potentially clogging or contaminating inhalants may be in use.

During an inhalation study, inhaled particles are deposited in different sites within the respiratory system. Potential deposition regions include the nose, the throat, the pharynx, the larynx, the large airways, the small airways, and the alveolar region.

Location of particle deposition can play a significant role in the biological effects of an inhalant. For example, high deposition of a pollutant may pose an increased health risk if it occurs in the small airways compared to deposition of that same pollutant in the large airways. Conversely, an inhaled drug may demonstrate a greater benefit if it is delivered to alveolar region instead of to the small airways. Thus it may be beneficial to control particle deposition during an inhalation study.

Both size and flow velocity of the inhalant particle can affect the region of deposition within the respiratory system. Generally, the smaller the particle size the more peripheral the deposition of the inhalant. For smaller particles, the velocity of the particle may also be an important factor in regional deposition within the respiratory system.

Inhalant flow velocity may be influenced by the respiratory patterns of a test subject. Thus different respiratory patterns may produce variation in respiratory deposition sites especially if small particle inhalants are used. This situation can produce inconsistent results particularly if the variation in respiratory patterns between test subjects is substantial. Thus it may be beneficial for an inhalant test system to provide the ability to adjust inhalant particle size in response to different respiratory patterns, during an inhalation study, in an attempt to maintain a consistent deposition site.

It is also true during an inhalation study that the inhalant flow velocity changes throughout the normal inspiratory phase of a test subject. Thus, inhalants may be deposited to different respiratory sites during normal inspiration. This fact may be used to facilitate targeted deposition of an inhalant to different respiratory sites by increasing the concentration of inhalant, for example in bolus fashion, at a certain time within the inspiratory phase of the respiratory cycle during an inhalation study. Consistency of deposition could also be maintained by adjusting the timing of this increase within the inspiratory phase.

Real-time respiratory measurements, during an inhalation study, may be used in an inhalant system to accomplish the following: (1) change the inhalant particle size after an initial target dose is achieved in a particular location of the respiratory system in order to facilitate delivery of a subsequent dose to a different target site in the respiratory system of the same test subject, (2) change the inhalant particle size based on a test subject's breathing pattern to facilitate consistent delivery of an inhaled substance to a specific target site in the respiratory system of that test subject, and (3) alter inhalant concentration at a particular time within the measured real-time inspiratory phase of the respiratory cycle in an effort to deliver an inhalant to a desired site within the test subject's respiratory system during an inhalation study. Timing within the inspiratory phase could also be adjusted to maintain a consistent deposition site if the test subject's respiratory pattern changed or to maintain consistency between different test subjects within an inhalation study.

FIG. 9 is a flow diagram of an example process 900 for changing the particle size of an inhalant to target delivery of the inhalant to a specific target site. In some implementations, the process 900 may be the inhalant testing procedure 630 included in the example overall testing process of FIG. 6. The process 900 starts in operation 905 where airborne inhalant is supplied in a chamber airway. For example, the inhalant may be supplied into the test chamber by a nebulizer connected to an air supply for the test chamber. In another example, the airborne inhalant may be supplied into the test chamber through a showerhead, which aerosolizes the inhalant into the air enclosed within the test chamber.

Impedance values are measured as the test subject breathes in operation 910. These measurements are used to determine an impedance difference measure for each breath, and this difference measure may either be determined in the device implanted in or worn by the test subject, or in external equipment. The impedance measures or impedance difference measures, as the case may be, may be wirelessly transmitted from the device implanted or externally worn by the test subject to the external receiver and processing equipment, where impedance difference measures may be stored in memory of the external equipment. This external equipment, again, may be components 130 and 135 of the example system shown in FIG. 1.

The impedance difference measure is then processed by the external equipment to provide an up-to-date (that is, real time) measure of cumulative respiratory volume and/or the dosage of inhalant substance taken in by the subject as the test proceeds. To do this, the external processing equipment performs a calculation in which the previously determined conversion factor or equation (e.g., the conversion factor stored in memory, in operation 770, during the calibration process 700) is then applied, at operation 915, to the impedance difference measure to determine a breath volume for the respiration cycle corresponding to the impedance difference measure. In other words, the volume taken in for a single breath may be determined from the impedance difference for that breath (from a point before the test subject begins to breathe in to a point at which the volume taken in the lungs is at its maximum for that cycle) and the stored calibration factor or equation.

An inspired dosage may then be calculated or determined, at step 920. This may be performed, for example, by applying various factors to the volume measure for the current respiration cycle, to determine an incremental dosage inspired for only that respiration cycle, and adding that to a running cumulative dosage value. The factors that are applied to the respiration volume for a particular respiration cycle may change over the course of a test, for example, because as the test progresses less dosage may be inspired for the same respiration volume. More specifically, the respiration volume for a respiration cycle, as determined in operation 920, may be multiplied by one or more factors including, but not limited to, inhalant concentration and a term that accounts for the amount of substance absorbed by the test subject (e.g., coefficient of absorption). In some implementations, dosimetry may be further refined by utilizing multiple absorption coefficients associated with various volumes of inspired inhalant. For example, changes in inhalant deposition in the respiratory tract, caused by varying ratios of inhalant in the lung to inhalant in dead spaces like the mouth and throat, can be reconciled.

The inspired dosage is then totaled in operation 925. For example, as the test subject breathes, the dosages determined, in operation 920, to have been inspired in each breath are summed over time to produce a cumulative dose measurement of the inhalant. If the total inspired dosage is determined, in operation 930, to be less than a predetermined total dosage, then, in operation 935, the converted measurements are used to assess the test subject's respiratory pattern. If at step 940 it is determined that an adjustment to the inhalant particle size is needed, then the inhalant particle size is modified in step 945. For example, the operation 935 can assess whether the test subject is taking shallow breaths or is breathing deeply, and this assessment along with information about the size of the inhalant particles being delivered to the test subject can be used to determine which tissues or regions of the respiratory tract that the inhalant is being delivered to. By adjusting the size of the inhalant particles, the delivery of the inhalant can be targeted to specific tissues or regions within the test subject's respiratory tract.

Once the particle size adjustment is made or if no particle size adjustment is necessary, the airborne inhalant continues to be supplied, at 905 in the process, in the chamber airway.

Else, if the total inspired dosage is determined, in operation 930, to be equal to or greater than the predetermined total dosage, an event may be triggered, in operation 950. For example, once the predetermined dose has been reached or exceeded, the inhalant supply may be altered or halted, or a notification or alarm may be raised. In another example, once the predetermined dose has been reached or exceeded, the test process 900 may be repeated with a different inhalant, possibly with a different target dosage.

FIG. 10 is a flow diagram of an example process 1000 for adjusting inhalant concentration during the inspiratory phase of the respiratory cycle. In some implementations, the process 1000 may be the inhalant testing procedure 630 included in the example overall testing process of FIG. 6. The process 1000 starts in operation 1005 where airborne inhalant is supplied in a chamber airway. For example, the inhalant may be supplied into the test chamber by a nebulizer connected to an air supply for the test chamber. In another example, the airborne inhalant may be supplied into the test chamber through a showerhead, which aerosolizes the inhalant into the air enclosed within the test chamber.

Impedance values are measured as the test subject breathes in operation 1010. These measurements are used to determine an impedance difference measure for each breath, and this difference measure may either be determined in the device implanted in or worn by the test subject, or in external equipment. The impedance measures or impedance difference measures, as the case may be, may be wirelessly transmitted from the device implanted or externally worn by the test subject to the external receiver and processing equipment, where impedance difference measures may be stored in memory of the external equipment. This external equipment, again, may be components 130 and 135 of the example system shown in FIG. 1.

In operation 1015, the impedance measurements are used to assess the phase of the test subject's respiratory cycle. If at step 1020 it is determined that an inhalant bolus is desired, due to the relative timing within the respiratory cycle, then the bolus is delivered in step 1025 to increase inhalant concentration within the chamber. For example, it may be desirable to deliver a bolus of inhalant near the time of peak inspiratory flow in order to preferentially facilitate delivery of an inhalant to, for example, the alveolar region of the lungs.

If no bolus increase is required at step 1020, then the impedance difference measure is processed by the external equipment to provide an up-to-date (that is, real time) measure of cumulative respiratory volume and/or the dosage of inhalant substance taken in by the subject as the test proceeds. To do this, the external processing equipment performs a calculation in which the previously determined conversion factor or equation (e.g., the conversion factor stored in memory, in operation 770, during the calibration process 700) is then applied, at operation 1030, to the impedance difference measure to determine a breath volume for the respiration cycle corresponding to the impedance difference measure. In other words, the volume taken in for a single breath may be determined from the impedance difference for that breath (from a point before the test subject begins to breathe in to a point at which the volume taken in the lungs is at its maximum for that cycle) and the stored calibration factor or equation. In operation 1035 the inspired dosage is determined. This may be performed, for example, by applying various factors to the volume measure for the current respiration cycle, to determine an incremental dosage inspired for only that respiration cycle, and adding that to a running cumulative dosage value. The factors that are applied to the respiration volume for a particular respiration cycle may change over the course of a test, for example, because as the test progresses less dosage may be inspired for the same respiration volume.

The inspired dosage is then totaled in operation 1040. For example, as the test subject breathes, the dosages determined, in operation 1035, to have been inspired in each breath are summed over time to produce a cumulative dose measurement of the inhalant. If the total inspired dosage is determined, in operation 1045, to be less than a predetermined total dosage, then the airborne inhalant continues to be supplied, at 1005 in the process, in the chamber airway. For example, the object if the testing process may be to deliver 150 cc of a drug to the test subject via respiratory administration, however if less than 150 cc has been determined, in operation 1045, to have been inspired by the test subject at the time of the determination in operation 1045, the test may continue running.

Else, if the total inspired dosage is determined, in operation 1045, to be equal to or greater than the predetermined total dosage, an event may be triggered, in operation 1050. For example, once the predetermined dose has been reached or exceeded, the inhalant supply may be altered or halted, or a notification or alarm may be raised. In another example, once the predetermined dose has been reached or exceeded, the test process 1000 may be repeated with a different inhalant, possibly with a different target dosage.

FIG. 11 is a block diagram of example external receiving and processing circuitry 1100 that may be used in executing the disclosed calibration and testing processes. In some implementations, the circuitry 1100 may be the receiving and processing component 135 and/or the computing system 130 of FIG. 1. The circuitry 1100 includes a calibration module 1110, a test procedure module 1120, and a processor 1130. In some implementations, the processor 1130 can be an electronic module specifically designed for use in the circuit 1100. In some other implementations, the processor 1100 can be a general-purpose processor such as computer processor (e.g., the CPU of a personal computer), a field programmable gate array (FPGA), or other form of general purpose electronic processor.

The calibration module 1110 is executed by the processor 1130 to compare respiratory volumetric measurements, such as those obtained from a pneumotachograph, to physiologic measurements, such as thoracic impedances, to determine correlations and/or equations that can be used to convert physiologic measurements to their volumetric equivalents. For example, the calibration module 1110 may perform the functions included in the calibration process 700.

The calibration module 1110 receives volumetric as well as impedance and/or RIP measurements from a data transceiver 1140. The data transceiver 1140 is configured to communicably connect to external devices such as the pneumotachograph 115, and a physiological sensing device, such as the system 200 or the device 300, connected to a test subject. In some embodiments, the data transceiver 1140 can connect to the external devices via a communications port 1142 and/or a wireless transceiver 1144. Once the calibration module 1110 has collected a number of substantially simultaneously sampled volumetric and physiological respiratory measurements, the calibration module 1110 determines a calibration formula 1150 and stores it in a memory 1160. In some implementations, the memory 1160 may be a random access memory, a FLASH memory, or other form of memory that can be accessed by the processor 1130.

The test procedure module 1120 is then executed by the processor 1130. The test procedure module 1120 performs the functions associated with a drug inhalation test, such as the test process 800. The test procedure module 1120 uses the calibration formula 1150 to convert measured physiological parameters received from the data transceiver 1140 (e.g., thoracic impedance or RIP) to equivalent volumetric values. As the test subject breathes, the test procedure module 1120 determines the volume of air inspired by the test subject, as well as a cumulative respiration volume 1170 that is stored in the memory 1160. In some implementations, the cumulative respiration volume 1170 can be used by the test procedure module 1120 to determine a total dose of inhalant inspired by the test subject. For example, a conversion factor (e.g., a ratio or mathematical formula) can be used to determine the amount of inhalant delivered to the test subject for a measured volume of inspired air on either a per-breath or cumulative basis. Thus, by determining the cumulative respiration volume 1170, the corresponding cumulative inspired dosage of inhalant can also be determined.

In some embodiments, the calibration formula 1150 and/or the cumulative respiration volume 1170 may also be persisted in a storage module 1180. For example, the storage module 1180 may be a hard disk drive, FLASH ram, an optical disk, a SAN, or other form of persistent memory.

Figure 12:
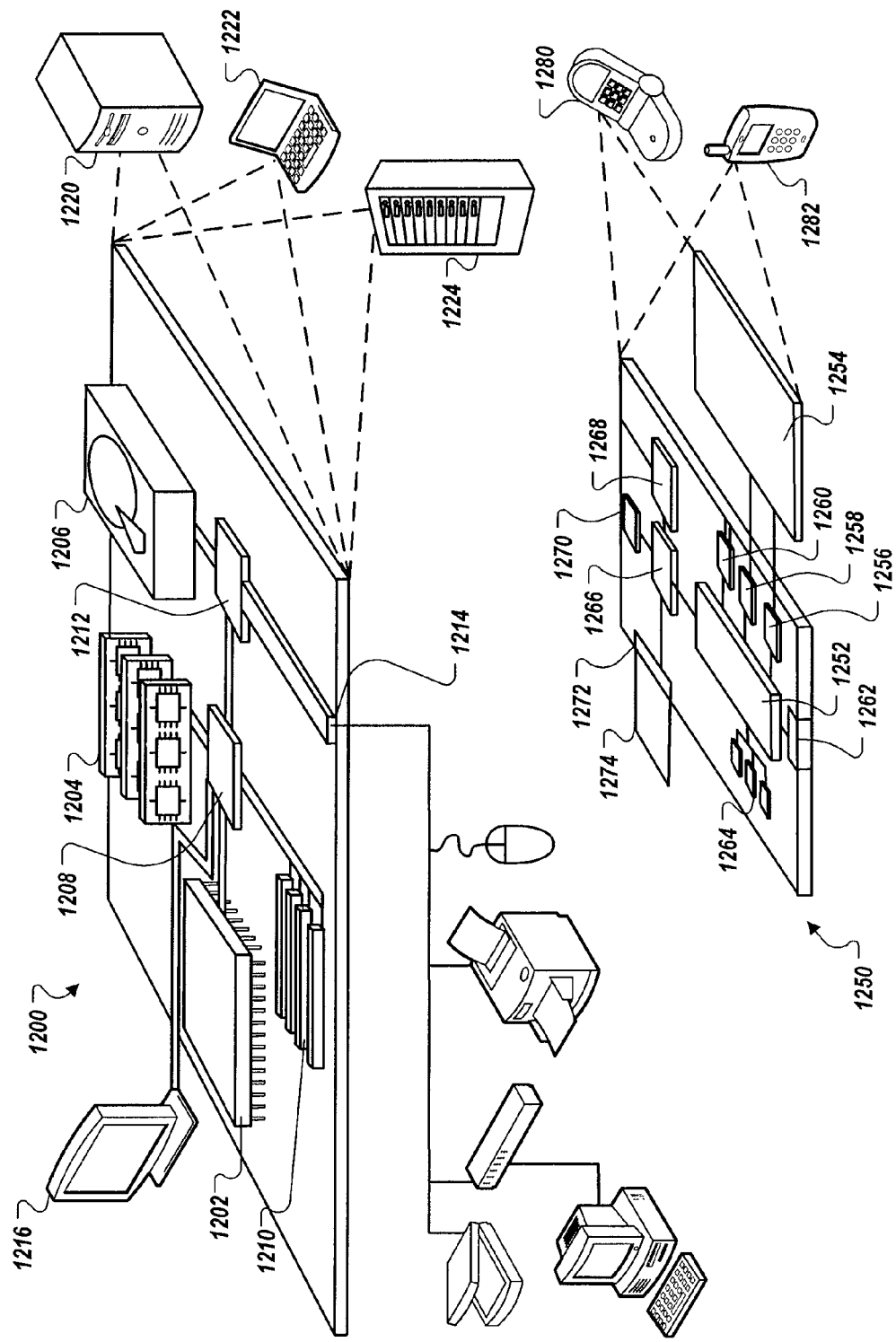

FIG. 12 is a block diagram of computing devices 1200, 1250 that may be used to implement the systems and methods described in this document, either as a client or as a server or plurality of servers. For example, the computing devices 1200, 1250 may perform the functions of the automated inhalation exposure system 130, the external ambulatory animal monitoring system 200, example implantable, wireless respiratory monitoring device 300, or the external receiving and processing circuitry 1120. Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a computer-readable medium. In one implementation, the memory 1204 is a volatile memory unit or units. In another implementation, the memory 1204 is a non-volatile memory unit or units.

The storage device 1206 is capable of providing mass storage for the computing device 1200. In one implementation, the storage device 1206 is a computer-readable medium. In various different implementations, the storage device 1206 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 1204, the storage device 1206, memory on processor 1202, or a propagated signal.

The high speed controller 1208 manages bandwidth-intensive operations for the computing device 1200, while the low speed controller 1212 manages lower bandwidth-intensive operations. Such allocation of duties is exemplary only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can process instructions for execution within the computing device 1250, including instructions stored in the memory 1264. The processor may also include separate analog and digital processors. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT LCD display or an OLED display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may be provide in communication with processor 1252, so as to enable near area communication of device 1250 with other devices. External interface 1262 may provide, for example, for wired communication (e.g., via a docking procedure) or for wireless communication (e.g., via Bluetooth or other such technologies).

The memory 1264 stores information within the computing device 1250. In one implementation, the memory 1264 is a computer-readable medium. In one implementation, the memory 1264 is a volatile memory unit or units. In another implementation, the memory 1264 is a non-volatile memory unit or units. Expansion memory 1274 may also be provided and connected to device 1250 through expansion interface 1272, which may include, for example, a SIMM card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provide as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, memory on processor 1252, or a propagated signal.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS receiver module 1270 may provide additional wireless data to device 1250, which may be used as appropriate by applications running on device 1250.

Device 1250 may also communicate audibly using audio codec 1260, which may receive spoken information from a user and convert it to usable digital information. Audio codex 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back-end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments of the invention have been described. Nevertheless, it will be understood that various modifications may be made without departing from the spirit and scope of the invention. For example, various forms of the flows shown above may be used, with steps re-ordered, added, or removed. Also, although several applications of the payment systems and methods have been described, it should be recognized that numerous other applications are contemplated. Accordingly, other embodiments are within the scope of the following claims.

What is claimed is:

1. A method of performing an inhalation test on a test subject, the method comprising:
    performing a calibration procedure comprising a) collecting respiration-related measurements for each of multiple respiration cycles from the test subject using a sensing device applied directly to the test subject, b) collecting corresponding respiration volume measurements for each of the multiple respiration cycles of the test subject by sensing atmospheric changes of a volume within a chamber in which the test subject is at least partially confined, and c) using the collected respiration-related and respiration volume measurements to calculate a calibration formula that correlates respiration-related measurements collected using the sensing device applied directly to the test subject to respiration volume measurements;
    performing an inhalation test on the test subject, during the inhalation test the test subject is at least partially confined within a test chamber and an inhalant substance is provided into the test chamber, wherein performing the inhalation test comprises a) collecting during the course of the inhalation test respiration-related measurements for respiration cycles of the test subject using the sensing device applied directly to the test subject, b) applying the calibration formula to the respiration-related measurements as they are collected during the inhalation test to determine, during the course of the inhalation test, a running measure of cumulative respiration volume for the test subject, and c) storing the running measure in computer storage memory.

2. The method of claim 1, wherein the sensing device applied directly to the test subject comprises a monitoring system comprising electrodes positioned to make impedance measurements across or around a portion of the lungs of the test subject.

3. The method of claim 1, wherein the sensing device applied directly to the test subject is implanted within the test subject and comprises:
    electrodes positioned to make impedance measurements across or around a portion of the lungs of the test subject; and
    a wireless transmitter to transmit the collected respiration-related measurements to external processing equipment.

4. The method of claim 1, wherein the sensing device applied directly to the test subject is worn by the test subject, and comprises:
    electrodes positioned on the test subject to make impedance measurements across or around a portion of the lungs of the test subject; and
    a wireless transmitter to transmit the collected respiration-related measurements to external processing equipment.

5. The method of claim 1, wherein the sensing device applied directly to the test subject is worn by the test subject, and comprises:
    Elastic bands positioned on the test subject to make expansion measurements across a portion of the lungs or abdomen of the test subject; and
    a wireless transmitter to transmit the collected respiration-related measurements to external processing equipment.

6. The method of claim 1, wherein the respiration volume measurements collected during the calibration procedure are made using a pneumotachograph or other suitable spirometer.

7. The method of claim 1, wherein the calculation of the calibration formula comprises performing a best-fit process of the collected measurements forming a relationship between the collected respiration-related measurements and the collected respiration volume measurements, wherein a formula for the relationship is the calibration formula.

8. The method of claim 1, wherein the performing of the inhalation test further comprises calculating for each respiration cycle a respiration volume measure for that cycle using the respiration-related measurement for that cycle and applying the calibration formula to that respiration-related measurement, and summing calculated respiration volume measurements for each cycle to provide the running measure of cumulative respiration volume for the test subject.

9. The method of claim 1, further comprising determining during the course of the inhalation test a running measure of cumulative dosage of inhalant substance inspired by the test subject.

10. The method of claim 9, further comprising calculating for each respiration cycle a dosage inspired for that cycle using a respiration volume measurement for that cycle, and summing calculated dosage measurements for each cycle to provide the running measure of the cumulative dosage inspired.

11. The method of claim 1, wherein the performing of the inhalation test further comprises:
    comparing the running measure of cumulative respiration volume to a selected threshold value; and
    triggering a predefined action to occur if the running measure of cumulative respiration volume reaches the selected threshold value.

12. The method of claim 11, wherein the predefined action comprises at least one of discontinuing providing the inhalant substance into the test chamber, changing a concentration of the inhalant substance being provided into the test chamber, changing a volume of the inhalant substance being provided into the test chamber, or changing a pressure in the test chamber.

13. The method of claim 11, wherein the predefined action comprises at least one of providing an indication of the threshold having been reached, and marking a point in time at which the threshold is first reached.

14. The method of claim 1, further comprising monitoring a physiological attribute of the test subject, and correlating a specified state of the physiological attribute with the value of the running measure of the cumulative respiration volume at the time the specified state of the physiological attribute was detected.

15. A monitoring system for use during an inhalation test on a test subject, the monitoring system comprising:
- a processor device;
- a test chamber configured to at least partially confine the test subject;
- a sensing device adapted to be applied directly to the test subject for measuring respiration-related measurements; and
- a test chamber sensing device configured to sense atmospheric changes of a volume within the test chamber;

wherein the processing device further comprises:
- a calibration processing module programmed to a) receive respiration-related measurements for each of multiple respiration cycles taken from the test subject using the sensing device adapted to be applied directly to the test subject, b) receive separate corresponding respiration volume measurements for each of the multiple respiration cycles of the test subject determined by the test chamber sensing device configured to sense atmospheric changes of a volume within the test chamber, c) use the received respiration-related and respiration volume measurements to calculate a calibration formula that correlates respiration-related measurements received using the sensing device adapted to be applied directly to the test subject to respiration volume measurements, and d) store the calibration formula in memory of the monitoring system; and
- a test procedure processing module programmed to a) receive during the course of an inhalation test respiration-related measurements for respiration cycles of the test subject using the sensing device adapted to be applied directly to the test subject, b) applying the stored calibration formula to the respiration-related measurements as they are collected during the inhalation test to determine, during the course of the inhalation test, a running measure of cumulative respiration volume for the test subject, and c) storing the running measure in memory of the monitoring system;

wherein the test procedure processing module is configured to perform the inhalation test on the test subject, and during the inhalation test the test subject is at least partially confined within the test chamber and an inhalant substance is provided into the test chamber.

16. The monitoring system of claim 15, wherein the calibration processing module is further programmed to perform a best-fit process of the received measurements forming a relationship between the received respiration-related measurements and the received respiration volume measurements, wherein a formula for the relationship is the stored calibration formula.

17. The monitoring system of claim 15, wherein the test procedure processing module is further programmed to:
- calculate for each respiration cycle a respiration volume measure for that cycle using the respiration-related measurement for that cycle and apply the stored calibration formula to that respiration-related measurement; and
- sum calculated respiration volume measurements for each cycle to provide the running measure of cumulative respiration volume for the test subject.

18. The monitoring system of claim 15, wherein the test procedure processing module is further programmed to determine during the course of an inhalation test a running measure of cumulative dosage of inhalant substance inspired by the test subject.

19. The monitoring system of claim 18, wherein the test procedure processing module is further programmed to:
- calculate for each respiration cycle a dosage inspired for that cycle using a respiration volume measurement for that cycle; and
- sum calculated dosage measurements for each cycle to provide the running measure of the cumulative dosage inspired.

20. The monitoring system of claim 15, wherein the test procedure processing module is further programmed to:
- compare the running measure of cumulative respiration volume to a selected threshold value; and
- trigger a predefined action to occur if the running measure of cumulative respiration volume reaches the selected threshold value.

21. The monitoring system of claim 15, wherein the specified action comprises at least one of discontinuing providing the inhalant substance into the test chamber, changing a concentration of the inhalant substance being provided into the test chamber, changing a volume of the inhalant substance being provided into the test chamber, or changing a pressure in the test chamber.

* * * * *